US008283158B2

(12) United States Patent
Emmert-Buck et al.

(10) Patent No.: US 8,283,158 B2
(45) Date of Patent: Oct. 9, 2012

(54) METHOD AND APPARATUS FOR PERFORMING MULTIPLE SIMULTANEOUS MANIPULATIONS OF BIOMOLECULES IN A TWO DIMENSIONAL ARRAY

(75) Inventors: Michael R. Emmert-Buck, Philadelphia, PA (US); Rodrigo F. Chuaqui, North Potomac, MD (US); Michael A. Tangrea, Odenton, MD (US)

(73) Assignee: The United States of America, as represented by the Secretary, Department of Health and Human Services, Rockville, MD (US)

( * ) Notice: Subject to any disclaimer, the term of this patent is extended or adjusted under 35 U.S.C. 154(b) by 0 days.

(21) Appl. No.: 12/587,976

(22) Filed: Oct. 14, 2009

(65) Prior Publication Data

US 2010/0105056 A1 Apr. 29, 2010

Related U.S. Application Data

(63) Continuation of application No. 10/535,521, filed as application No. PCT/US03/37208 on Nov. 20, 2003, now abandoned.

(60) Provisional application No. 60/428,754, filed on Nov. 25, 2002.

(51) Int. Cl.
*C12M 1/34* (2006.01)
(52) U.S. Cl. .................................... 435/288.4; 435/91.2
(58) Field of Classification Search ........................ None
See application file for complete search history.

(56) References Cited

U.S. PATENT DOCUMENTS

| | | | |
|---|---|---|---|
| 3,620,947 | A | 11/1971 | Allen et al. |
| 4,176,069 | A | 11/1979 | Metz et al. |
| 4,337,131 | A | 6/1982 | Vesterberg |
| 4,613,567 | A | 9/1986 | Yasoshima et al. |
| 4,716,101 | A | 12/1987 | Thompson et al. |
| 4,795,562 | A | 1/1989 | Walsh |
| 4,840,714 | A | 6/1989 | Littlehales |
| 4,874,691 | A | 10/1989 | Chandler |
| 5,047,135 | A | 9/1991 | Nieman |
| 5,057,438 | A | 10/1991 | Imai et al. |
| 5,078,853 | A | 1/1992 | Manning et al. |
| 5,155,049 | A | 10/1992 | Kauvar et al. |
| 5,173,159 | A | 12/1992 | Dutertre |
| 5,238,651 | A | 8/1993 | Chuba |
| 5,332,484 | A | 7/1994 | Hilt |
| 5,387,325 | A | 2/1995 | Opplt |

(Continued)

FOREIGN PATENT DOCUMENTS

EP 0139373 5/1985

(Continued)

OTHER PUBLICATIONS

Nuovo (2001) The J. of Histochemistry & Cytochemistry vol. 49 (11): 1329-1339.*

(Continued)

*Primary Examiner* — Samuel Woolwine
*Assistant Examiner* — Suchira Pande
(74) *Attorney, Agent, or Firm* — Klarquist Sparkman, LLP

(57) ABSTRACT

This invention relates to methods and apparati for performing multiple simultaneous manipulations of biomolecules in a two-dimensional array, such as a gel, membrane, tissue biopsy, etc. Such manipulations particularly include assays and nucleic acid amplification protocols.

12 Claims, 6 Drawing Sheets

U.S. PATENT DOCUMENTS

| | | | |
|---|---|---|---|
| 5,427,664 | A | 6/1995 | Stoev et al. |
| 5,438,128 | A | 8/1995 | Nieuwkerk et al. |
| 5,486,452 | A | 1/1996 | Gordon et al. |
| 5,650,055 | A | 7/1997 | Margolis |
| 5,679,310 | A | 10/1997 | Manns |
| 5,716,508 | A | 2/1998 | Starr |
| 5,741,639 | A | 4/1998 | Ensing et al. |
| 5,843,657 | A | 12/1998 | Liotta et al. |
| 5,993,627 | A | 11/1999 | Anderson et al. |
| 6,013,165 | A | 1/2000 | Wiktorowicz et al. |
| 6,064,754 | A | 5/2000 | Parekh et al. |
| 6,087,134 | A | 7/2000 | Saunders |
| 6,135,942 | A | 10/2000 | Leptin |
| 6,221,600 | B1 | 4/2001 | MacLeod et al. |
| 6,232,067 | B1 | 5/2001 | Hunkapiller et al. |
| 6,303,308 | B1 | 10/2001 | Halle et al. |
| 6,461,814 | B1 | 10/2002 | Spinella |
| 6,969,615 | B2 * | 11/2005 | Knezevic et al. ............ 436/518 |
| 2001/0044104 | A1 | 11/2001 | Warrington et al. |
| 2002/0012920 | A1 | 1/2002 | Gardner et al. |
| 2002/0168643 | A1 * | 11/2002 | Wierzbowski et al. ........... 435/6 |
| 2003/0027142 | A1 | 2/2003 | Ishiguro et al. |
| 2003/0157523 | A1 * | 8/2003 | Frantz et al. ...................... 435/6 |
| 2004/0053326 | A1 | 3/2004 | Emmert-Buck et al. |
| 2004/0081979 | A1 | 4/2004 | Knezevic et al. |
| 2004/0081987 | A1 | 4/2004 | Knezevic et al. |
| 2005/0064486 | A1 | 3/2005 | Ishiguro et al. |

FOREIGN PATENT DOCUMENTS

| | | |
|---|---|---|
| EP | 0525723 | 2/1993 |
| EP | 1174521 | 1/2002 |
| WO | WO/9832847 | 1/1998 |
| WO | WO 98/20353 | 5/1998 |
| WO | WO 98/41863 | 9/1998 |
| WO | WO 99/67647 | 12/1999 |
| WO | WO 00/45168 | 8/2000 |
| WO | WO/0077214 | 12/2000 |
| WO | WO/0138577 | 5/2001 |
| WO | WO/0210449 | 2/2002 |
| WO | WO/0246465 | 6/2002 |
| WO | WO/02068466 | 9/2002 |

OTHER PUBLICATIONS

Burke et al. (1991) Mammalian Genome vol. 1:65.*

Aldaz et al., "Serial Analysis of Gene Expression in Normal P53 Null Mammary Epithelium", *Oncogene*, vol. 21, pp. 6366-6376, 2002.

Anisimov et al., "A Quantitative and Validated Sage Transcriptome Reference for Adult Mouse Heart", *Genomics*, vol. 80, pp. 213-222, 2002.

Bono et al., "Functional Transcriptomes: Comparative Analysis of Biological Pathways and Processes in Eukaryotes to Infer Genetic Networks Among Transcripts", *Curr. Opin. Struct. Biol.*, vol. 12, pp. 355-361, 2002.

Braun and Abraham, "Modified diffusion blotting for rapid and efficient protein transfer with PhastSystem", *Electrophoresis*, vol. 10, pp. 249-253, 1989.

Cleeve et al., "Isoelectric focusing of human tissue alkaline phosphatase isoenzymes in agarose gel", *Clinica Chimica Acia*, vol. 137, pp. 333-340, 1984.

Curtis et al., "Control Analysis of DNA Microarray Expression Data", *Molec. Biol. Rep.*, vol. 29, pp. 67-71, 2002.

Demczuk et al., "Identification and analysis of all components of a gel retardation assay by combination with immunoblotting", *Proc. Natl. Acad. Sci. U.S.A.*, vol. 90, pp. 2574-2578, 1993.

Devaux, "Transcriptomes, Transcription Activators and Microarrays", *FEBS Lett.*, vol. 498, pp. 140-144, 2001.

Englert et al., "Layered Expression Scanning: Rapid Molecular Profiling of Tumor Samples", *Cancer Res.*, vol. 60, pp. 1526-1530, 2000.

Englert et al., "Molecular profiling of human cancer: New opportunities", *Curr. Opin. Mol. Therap.*, vol. 1, No. 6, pp. 712-719, 1999.

Evans et al., "Evaluation of Affymetrix Gene Chip Sensitivity in Rat Hippocampal Tissue Using Sage Analysis. Serial Expression of Gene Expression", *Eur. J. Neurosci.*, vol. 16, pp. 409-413, 2002.

Heukeshoven and Dernick, "Effective blotting of ultrathin polyacrylamide gels anchored to a solid matrix", *Electrophoresis*, vol. 16, pp. 748-756, 1995.

Inczédy-Marcsek et al., "Extraction of proteins within ultrathin-layer polyacrylamide electrophoresis (SDS-PAGE) and isoelectric focusing (PAGIF) of cryostat sections and tissue culture specimens", *Acta histochemica, Suppl.-Band XXXVI*, S. 377-394 1998.

Klein et al., "Combined Transcriptome and Genome Analysis of Single Micrometastatic Cells", *Natl. Biotechnol.*, vol. 20, pp. 387-392, 2002.

Kononen et al., "Tissue microarrays for high-throughput molecular profiling of tumor specimins", *Nature*, vol. 4, No. 7, pp. 844-847, 1998.

Legocki and Verma, "Multiple Immunoreplica Techique: Screening for Specific Proteins with a Series of Different Antibodies Using One Polyacrylamide Gel", *Anal. Biochem.* vol. 111, pp. 385-392, 1981.

Li et al., "Comparative Genome-scale Analysis of Gene Expression Profiles in T Cell Lymphoma Cells During Malignant Progression Using a Complementary DNA Microarray", *Amer. J. Pathol.*, vol. 158, pp. 1231-1237, 2001.

Manabe et al., "An Electroblotting Apparatus for Multiple Replica Technique and Identification of Human Serum Proteins on Micro Two-Dimensional Gels", *Anal. Biochem.*, vol. 143, pp. 39-45, 1984.

Neumann and Milliner, "Two replica blotting methods for fast immunological analysis of common proteins in two-dimensional electrophoresis", *Electrophoresis*, vol. 19, pp. 752-757, 1998.

Olsen and Wiker, "Diffusion blotting for rapid production of multiple identical imprints from sodium dodecyl sulfate polyacrylamide gel electrophoresis on a solid support", *J. Immunol. Methods*, vol. 220, pp. 77-84, 1998.

Pappalardo et al., "Microdissection, microchip arrays, and molecular analysis of tumor cells (Primary and Metastases)", *Seminars in Radiation Oncology*, vol. 8, No. 3, pp. 217-223, 1998.

Piper, M.D.W. et al., "Reproducibility of Oligonucleotide Microarray Transcriptome Analyses: An Interlaboratory Comparison Using Chemostat Cultures of *Saccharomyces Cerevisae*", *J. Biol. Chem.*, vol. 277, pp. 37001-37008, 2002.

Piquemal et al., "Transcriptome Analysis of Monocytic Leukemia Cell Differentiation", *Genomics*, vol. 80, No. 3, pp. 361-371, 2002.

Rutanen et al., "Induction of endometrial plasminogen activator-inhibitor 1: a possible mechanism contributing to the effect of intrauterine levonorgestrel in the treatment of menorrhagia", *Fertility and Sterility*, vol. 73, No. 5, pp. 1020-1024, 2000.

Saha et al., "Using the Transcriptome to Annotate the Genome", *Nat. Biotechnol.*, vol. 20, pp. 508-512, 2002.

Sanchez et al., "Simultaneous analysis of cyclin and oncogene expression using multiple monoclonal antibody immunoblots", *Electrophoresis*, vol. 18, pp. 638-641, 1997.

Schumacher and Trudrung, "Direct Tissue Isoelectric Focusing on Mini Ultrathin Polyacrylamide Gels followed by Subsequent Western Blotting, Enzyme Detection, and Lectin Labeling as a Tool for Enzyme Characterization in Histochemistry", *Analytical Biochemistry*, vol. 194, pp. 256-258, 1991.

Schumacher et al., "Direct tissue isoelectric focusing on ultrathin polyacrylamide gels. Applications in enzyme, lectin and immunohistochemistry", *Histochemical Journal*, vol. 22, pp. 433-438, 1990.

Su, et al., "Large-scale Analysis of the Human and Mouse Transcriptomes", *Proc. Natl. Acad. Sci. U.S.A.*, vol. 99, pp. 4465-4470, 2002.

Swaroop, et al., "Transcriptome Analysis of the Retina", *Genome Biol.*, vol. 30, No. 8: Reviews 1022, Epub 2002.

van der Sluis et al., "Immunochemical detection of peptides and proteins on press-blots after direct tissue gel isoelectric focusing", *Electrophoresis*, vol. 9, pp. 654-661, 1988.

* cited by examiner

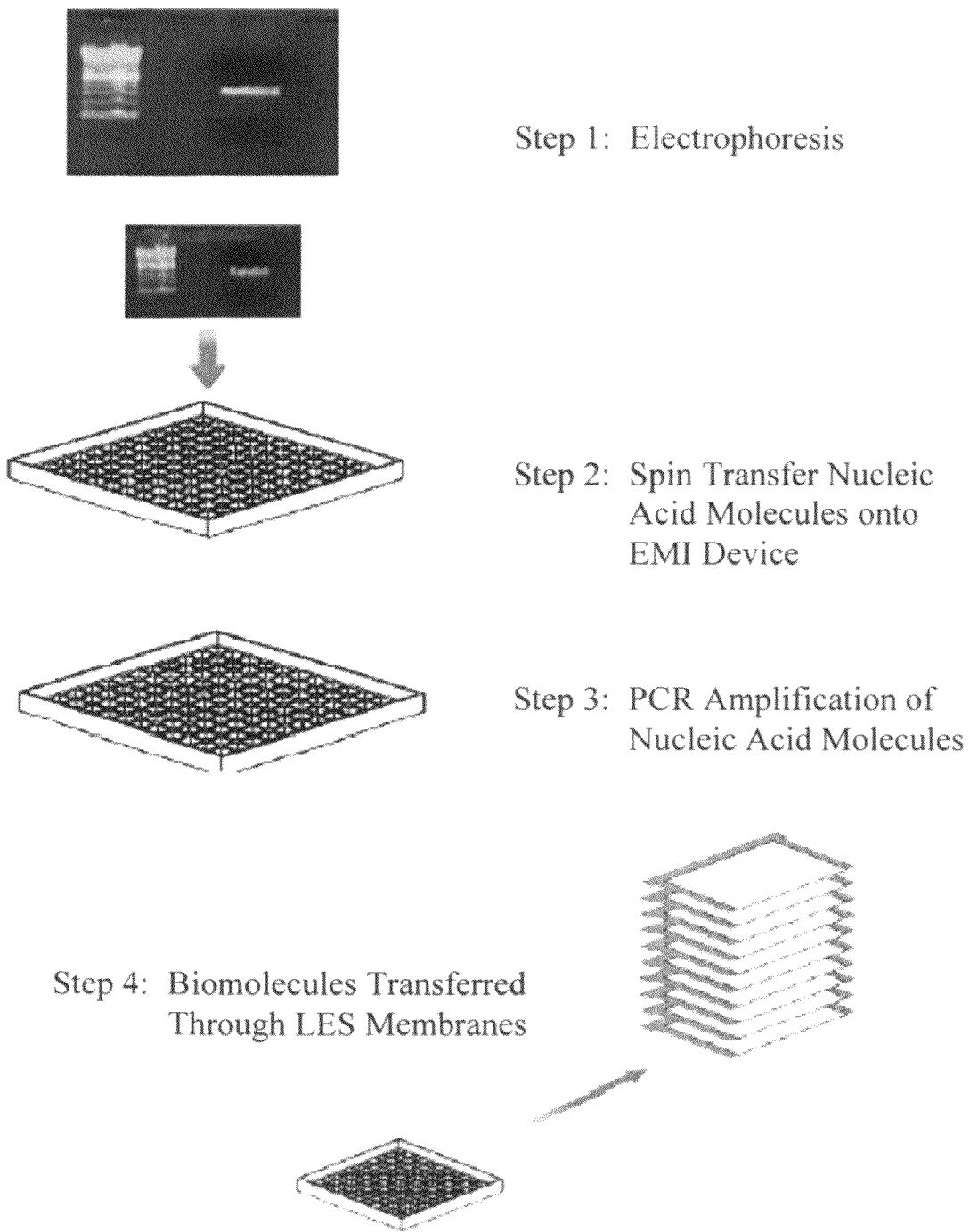

METHOD AND APPARATUS FOR PERFORMING MULTIPLE SIMULTANEOUS MANIPULATIONS OF BIOMOLECULES IN A TWO DIMENSIONAL ARRAY

CROSS-REFERENCE TO RELATED APPLICATIONS

This is a continuation of U.S. application Ser. No. 10/535,521, filed May 18, 2005 now abandoned, which is the U.S. National Stage of International Application No. PCT/US2003/037208, filed Nov. 20, 2003, which was published in English under PCT Article 21(2), and which claims the benefit of U.S. Provisional Application No. 60/428,754, filed Nov. 25, 2002. The entire disclosures of the prior applications are considered to be part of the disclosure of the accompanying application and are hereby incorporated by reference.

STATEMENT OF GOVERNMENTAL INTEREST

This invention was funded by the Intramural Research Program at the National Institutes of Health. The United States Government has certain rights to this invention.

FIELD OF THE INVENTION

This invention relates to methods and apparati for performing multiple simultaneous manipulations of biomolecules in a two-dimensional array, such as a gel, membrane, tissue biopsy, etc. Such manipulations particularly include assays and nucleic acid amplification protocols.

BACKGROUND OF THE INVENTION

An emerging approach to the investigation of disease and cellular state involves the analysis of the complete set of RNA molecules—the "transcriptome"—expressed by a cell or tissue sample (see, Devaux, F. (2001) "TRANSCRIPTOMES, TRANSCRIPTION ACTIVATORS AND MICROARRAYS," *FEBS Lett.* 498:140-4; see also, U.S. Pat. Nos. 6,221,600; 6,303,308; and 6,461,814; European Patent Publications Nos. EP 0970202a2; 1174521a3; and 1190044a2; Japanese Patent Application No. JP 2002142765a2, and PCT International Patent Publications Nos. WO 0077214a3; WO 0138577a3; WO 02068466a2; WO 0210449a2; WO 0246465a2 and WO 9832847a2).

High-throughput gene expression array and proteomic technologies make possible the simultaneous analysis of thousands of mRNA transcripts and proteins, allowing a global view of the molecular events associated with normal cellular processes and disease states (Schena, M. et al. (1995) "QUANTITATIVE MONITORING OF GENE EXPRESSION PATTERNS WITH A COMPLEMENTARY DNA MICROARRAY," *Science* 270: 467469; Schena, M. et al. (1998) "MICROARRAYS: BIOTECHNOLOGY'S DISCOVERY PLATFORM FOR FUNCTIONAL GENOMICS," *Trends Biotechnol.* 16: 301-306; DeRisi, J. et al. (1996) "USE OF A cDNA MICROARRAY TO ANALYSE GENE EXPRESSION PATTERNS IN HUMAN CANCER," *Nat. Genet.* 14: 457-460; Chee, M. et al. (1996) "ACCESSING GENETIC INFORMATION WITH HIGH-DENSITY DNA ARRAYS. *Science* 274: 610-614; Lander, E. (1999) "Array Of Hope." *Nat. Genet.* 21: 3-4; Emmert-Buck, M. R. et al. (2000) "A STRATEGIC APPROACH FOR PROTEOMIC ANALYSIS OF HUMAN TUMORS," *Mol. Carcin.* 27: 1-8; Emmert-Buck, M. R. et al. (2000) "MOLECULAR PROFILING OF CLINICAL TISSUE SPECIMENS: FEASIBILITY AND APPLICATIONS," *Am. J Pathol.* 156: 1109-1115; Celis, J. et al. (2000) "GENE EXPRESSION PROFILING: MONITORING TRANSCRIPTION AND TRANSLATION PRODUCTS USING DNA MICRO ARRAYS AND PROTEOMICS," *FEBS Lett.* 480: 2-16; Anderson, N. L. et al. (1998) "PROTEOME AND POTEOMICS: NEW TECHNOLOGIES, NEW CONCEPTS, AND NEW WORDS," *Electrophoresis* 19: 1853-1861; Duggan, D. J. et al. (1999) "EXPRESSION PROFILING USING cDNA MICROARRAYS," *Nat. Genet.* 21: 10-14; Khan, J. et al. (1999) "EXPRESSION PROFILING IN CANCER USING cDNA MICROARRAYS," Electrophoresis 20: 223-229; Lipshutz, R. J. et al. (1999) "HIGH DENSITY SYNTHETIC OLIGONUCLEOTIDE ARRAYS," *Nat. Genet.* 21: 20-24; Lockhart, D. I. et al. (1996) "EXPRESSION MONITORING BY HYBRIDIZATION TO HIGH-DENSITY OLIGONUCLEOTIDE ARRAYS," *Nat. Biotechnol.* 14: 1675-1680; Velculescu, V. et al. (1995) "SERIAL ANALYSIS OF GENE EXPRESSION," *Science* 270: 484-487; Liotta, L. et al. (2000) "MOLECULAR PROFILING OF HUMAN CANCER," *Nature Reviews Genetics* 1: 48-56).

The emergence of transcriptome analysis has, however, been encumbered by the limitations of existing methodologies. Typically, such technologies identify a subset of genes (from a few dozen to several hundred) whose expression profile provides novel insight into cellular physiology and/or allows disease states to be segregated on a molecular rather than a phenotypic basis (Perou, C. et al. (2000) "MOLECULAR PORTRAITS OF HUMAN BREAST TUMOURS," *Nature* 406: 747-752; Alizadeh, A. A. et al. (2000) "DISTINCT TYPES OF DIFFUSE LARGE B-CELL LYMPHOMA IDENTIFIED BY GENE EXPRESSION PROFILING," *Nature* 403: 503-511; Dhanasekaran, S. et al. (2001) "DELINEATION OF PROGNOSTIC BIOMARKERS IN PROSTATE CANCER," *Nature* 412: 822-826; Hedenfalk, I. et al. (2001) "GENE-EXPRESSION PROFILES IN HEREDITARY BREAST CANCER," *N Engl. J. Med.* 344: 539-548; Golub, T. R. et al. (1999) "MOLECULAR CLASSIFICATION OF CANCER: CLASS DISCOVERY AND CLASS PREDICTION BY GENE EXPRESSION MONITORING. *Science* 286:531-537; Klose, J. (1999) "GENOTYPES AND PHENOTYPES," *Electrophoresis* 20: 643-652; Strausberg, R. L. et al. (2000) "THE CANCER GENOME ANATOMY PROJECT: BUILDING AN ANNOTATED GENE INDEX," *Trends Genet.* 16:103-106; Zhang, L. et al. (1997) "GENE EXPRESSION PROFILES IN NORMAL AND CANCER CELLS," *Science* 276: 1268-1272). Although these studies provide valuable information, it is desirable to independently confirm and quantitatively measure the expression level of each of the genes of interest. Prior to the advent of the present invention, this represented a significant challenge in terms of time and effort. Moreover, the amount of biological sample available for subsequent investigation is often limiting, particularly in the case of developmental biology samples and clinical specimens.

Although transcriptome analysis can be conducted by performing multiple Northern blots (Aldaz, C. M. et al., (2002) "SERIAL ANALYSIS OF GENE EXPRESSION IN NORMAL p53 NULL MAMMARY EPITHELIUM," *Oncogene* 21:6366-6376), this approach can be laborious and time-consuming (see, Su, A. I. et al. (2002) "LARGE-SCALE ANALYSIS OF THE HUMAN AND MOUSE TRANSCRIPTOMES," *Proc. Natl. Acad. Sci USA* 99:4465-70). More fundamentally, such an analysis is inherently biased against low abundance transcripts.

Various protocols have likewise been developed to generate cDNA libraries from globally amplified RNA of single cells (Belyaysky, A et al. (1989) "PCR-BASED cDNA LIBRARY CONSTRUCTION: GENERAL cDNA LIBRARIES AT THE LEVEL OF A FEW CELLS," *Nucl. Acids Res.* 17:2919-2932; Brady, G. et al. (1993) "CONSTRUCTION OF cDNA LIBRARIES FROM SINGLE CELLS," *Meth. Enzymol.* 225:611-623; Karrer, E. E. et al. (1995) "IN SITU ISOLATION OF MRNA FROM INDIVIDUAL PLANT CELLS: CREATION OF CELL-SPECIFIC CDNA LIBRARIES," *Proc. Natl. Acad. Sci. USA* 92:3814-3818), and cDNA microarrays have been used to analyze gene expression patterns (DeRisi, J. et al. (1996) "USE OF A cDNA MICROARRAY TO ANALYSE GENE EXPRESSION PATTERNS IN HUMAN CANCER" *Nature Genetics* 14:457-60; Li, S. et al. (2001) "COMPARATIVE GENOME-SCALE ANALYSIS OF GENE EXPRESSION PROFILES IN T CELL LYMPHOMA CELLS DURING MALIGNANT PROGRESSION USING A COMPLEMENTARY DNA MICROARRAY," *Amer. J. Pathol.* 158:1231-1237; Saha, S. et al. (2002) "USING THE TRANSCRIPTOME TO ANNOTATE THE GENOME," *Nat. Biotechnol.* 20:508-512; Bono, H. et al. (2002) "FUNCTIONAL TRANSCRIPTOMES: COMPARATIVE ANALYSIS OF BIOLOGICAL PATHWAYS AND PROCESSES IN EUKARYOTES TO INFER GENETIC NETWORKS AMONG TRANSCRIPTS," *Curr Opin Struct Biol.* 12:355-361; Schena, M. et al. (1995) "QUANTITATIVE MONITORING OF GENE EXPRESSION PATTERNS WITH A COMPLEMENTARY DNA MICROARRAY" *Science* 270:467-70; Anisimov, S. et al. (2002) "A QUANTITATIVE AND VALIDATED SAGE TRANSCRIPTOME REFERENCE FOR ADULT MOUSE HEART," *Genomics* 80:213-222).

Unfortunately, however, all such protocols have drawbacks, including the selective amplification of the 3' ends of a transcript, insufficient sensitivity in amplification (Klein, C. A. et al. (2002) "COMBINED TRANSCRIPTOME AND GENOME ANALYSIS OF SINGLE MICROMETASTATIC CELLS," *Nat. Biotechnol.* 20:387-92) and the problem of distinguishing critical transcript species from merely abundant transcripts (Curtis, R. K. et al. (2002) "CONTROL ANALYSIS OF DNA MICROARRAY EXPRESSION DATA," *Mol. Biol. Rep.* 29:67-71). While microarrays permit one to compare transcriptomes of different cells and tissues, they do not retain information concerning the architecture or location of the detected transcripts. Techniques of in situ hybridization and amplification have been developed to permit the localization of RNA transcripts, however such techniques focus on one or a small number of genes and do not assess the expression of the transcriptome (see, e.g., Nuovo, G. J. (2001) "CO-LABELING USING IN SITU PCR: A REVIEW," *J. Histochem. Cytochem.* 49:1329-1339; Moore, J. G. et al. (2000) "HER-2/NEU GENE AMPLIFICATION IN BREAST IMPRINT CYTOLOGY ANALYZED BY FLUORESCENCE IN SITU HYBRIDIZATION: DIRECT COMPARISON WITH COMPANION TISSUE SECTIONS," *Diagn. Cytopathol.* 23:299-302; Seeds, M. C. et al. (2000) "CELL-SPECIFIC EXPRESSION OF GROUP X AND GROUP V SECRETORY PHOSPHOLIPASES A(2) IN HUMAN LUNG AIRWAY EPITHELIAL CELLS," *Amer. J. Respir. Cell. Mol. Biol.* 23:37-44).

Various approaches have been attempted to "capture" the 2-dimensional positional relationship between molecules of a sampled array. A paraffin block has been described (website with the host name of "cmag", domain name of "cit.nih.gov" and file extension "Tissuearray.htm) in which multiple cores (50-500) of tissue are placed in an organized grid. The device is a said to be amenable for use in a variety of experiments, including immunohistochemistry, immunofluorescence, FISH, in situ hybridization, and to provide a high throughput platform for tissue, in which hundreds of samples can be analyzed at one time, and multiple experiments can be performed on the same array (see, the website with the host name "www", domain name of "laborel.no", and file extension "Acrobat/Biogenex/Biolink%20VOL.pdf). Microwell and microtiter plates (e.g., Thermo Labsystems 384-Well Solid Microtiter Plate) are example of 2-dimensional arrays of partitioned grids or chambers.

The problem of detecting high relevance, low abundance, transcripts is of particular significance in the analysis of complex tissue samples. Advanced technologies, such as the "Gene Chip" are reportedly able to detect no more than 30% of the transcripts present in complex tissue samples (Evans, S. J. et al. (2002) "EVALUATION OF AFFYMETRIX GENE CHIP SENSITIVITY IN RAT HIPPOCAMPAL TISSUE USING SAGE ANALYSIS. SERIAL ANALYSIS OF GENE EXPRESSION," *Eur. J. Neurosci.* 16:409-13; Piper, M. D. W. et al. (2002) "REPRODUCIBILITY OF OLIGONUCLEOTIDE MICROARRAY TRANSCRIPTOME ANALYSES: AN INTERLABORATORY COMPARISON USING CHEMOSTAT CULTURES OF *SACCHAROMYCES CEREVISIAE*," *J. Biol. Chem.* 277:37001-37008).

Where relevant cells (i.e., those associated with the production of high relevance, low abundance, transcripts) can be identified, techniques such as microdissection or laser-capture microscopy may be employed (Emmert-Buck, M. R. et al. (1996) "LASER CAPTURE MICRODISSECTION," *Science* 274: 998-1001; Bonner, R. F. et al. (1997) "LASER CAPTURE MICRODISSECTION: MOLECULAR ANALYSIS OF TISSUE," *Science* 278: 1481-1483), however, in many cases such relevant cells have not been identified, or cannot be detected.

In particular, there is an important need for new technologies that facilitate follow-up analysis of array- and proteomic-derived data. Although many such approaches are under development each has its particular weaknesses (see, for example, Kononen, J. et al. (1998) "TISSUE MICRO ARRAYS FOR HIGH-THROUGHPUT MOLECULAR PROFILING OF TUMOR SPECIMENS," *Nat. Med.* 4: 844-847; Berndt, P. et al. (1999) "RELIABLE AUTOMATIC PROTEIN IDENTIFICATION FROM MATRIX-ASSISTED LASER DESORPTION/IONIZATION MASS SPECTROMETRIC PEPTIDE FINGERPRINTS," *Electrophoresis* 20: 3521-3526; Binz, P. A. et al. (1999) "A MOLECULAR SCANNER TO AUTOMATE PROTEOMIC RESEARCH AND TO DISPLAY PROTEOME IMAGES," *Anal. Chem.* 71: 4981-4988; Bubendorf, L. et al. (1999) "SURVEY OF GENE AMPLIFICATIONS DURING PROSTATE CANCER PROGRESSION BY HIGH-THROUGHOUT FLUORESCENCE IN SITU HYBRIDIZATION ON TISSUE MICROARRAYS," *Cancer Res.* 59: 803-806; Celis, J. E. et al. (1999) "2D PROTEIN ELECTROPHORESIS: CAN IT BE PERFECTED?" *Curr. Opin. Biotechnol.* 10:16-21; Humphery-Smith, I. (1998) "PROTEOMICS: FROM SMALL GENES TO HIGH-THROUGHPUT ROBOTICS," J. Protein Chem. 17:524-525; Herbert, B. (1999) "ADVANCES IN PROTEIN SOLUBILIZATION FOR TWO-DIMENSIONAL ELECTROPHORESIS," *Electrophoresis* 20: 660-663; Liu. Y. et al. (1999) "ACTIVITY-BASED PROTEIN PROFILING: THE SERINE HYDROLASES," *Proc. Natl. Acad. Sci. USA.* 96: 14694-14699; Lueking, A. et al. (1999) "PROTEIN MICRO ARRAYS FOR GENE EXPRESSION AND ANTIBODY SCREENING," *Anal. Biochem.* 270:103-111; Quadroni, M. et al. (1999) "PROTEOMICS AND AUTOMATION," *Electrophoresis* 20: 664-677; Yates, J. R., $3^{rd}$ (2000) "MASS SPECTROMETRY: FROM GENOMICS TO PROTEOMICS," *Trends Genet.* 16: 5-8; Sidransky, D. (2000) "EMERGING MOLECULAR MARKERS OF CANCER," *Nature Reviews Cancer* 2: 210-219).

Thus, despite all such advances, the development of a global amplification system remains "the most critical hurdle" to transcriptome analysis. (Klein, C. A. et al. (2002) "COMBINED TRANSCRIPTOME AND GENOME ANALYSIS OF SINGLE MICROMETASTATIC CELLS," *Nat. Biotechnol.* 20:387-92). A need thus remains for an apparatus and method that would permit multiple, preferably simultaneous, manipulations of the biomolecules present in a two-dimensional array, such as a gel, or other solid support. The present invention is directed to this and other needs.

SUMMARY OF THE INVENTION

This invention relates to methods and apparati for performing multiple simultaneous manipulations of biomolecules in a two-dimensional array, such as a gel, membrane, tissue biopsy, etc. Such manipulations particularly include assays and nucleic acid amplification protocols.

In detail, the invention concerns a method for analyzing the transcriptome of a cellular sample comprising analyzing two or more molecular species present in a 2-dimensional array of the cellular sample, wherein the method comprises treating the 2-dimensional array with an External Movement Inhibitor device having multiple discrete partitions, so as to sequester molecules present in the array into one or more discrete regions, wherein the treatment preserves the positional relationship of the molecules of the 2-dimensional array, and permits a determination of the location(s) in the cellular sample in which the molecular species are present.

The invention further concerns the embodiment of such method wherein the cellular sample is a cellular sample obtained from a mammal (especially wherein the mammal is a human).

The invention further concerns the embodiment of such methods wherein the cellular sample is a tissue sample (especially a biopsy).

The invention particularly concerns the embodiment of such methods wherein the molecular species are nucleic acid molecules. The invention further concerns the embodiment of such method wherein the method additionally comprises incubating the sequestered nucleic acid molecules of two or more regions under conditions sufficient to permit the manipulation of one or more preselected nucleic acid molecules if present at the regions, while preserving the positional relationship of the molecules relative to other molecules of the 2-dimensional array. The invention further concerns the embodiment of such method wherein the method comprises incubating the sequestered nucleic acid molecules of all of the regions under conditions sufficient to permit the manipulation of the one or more preselected nucleic acid molecules. The invention further concerns the embodiment of such methods wherein the method additionally comprises transferring the manipulated nucleic acid species to two or more membranes, the membranes being differentially treated to enable the determination of the location(s) of manipulated nucleic acid species. The invention further concerns the embodiment of such methods wherein the manipulation is selected from the group consisting of nucleic acid amplification, reverse transcription, labeling, cloning, and the assaying of a biomolecule. The invention further concerns the embodiment of such methods wherein one or more of the preselected nucleic acid molecule(s) are diagnostic of a disease state and/or wherein the nucleic acid molecules are amplified using a polymerase chain reaction.

The invention further concerns the embodiment of such methods wherein the cellular sample is an extract of a cell, and the 2-dimensional array is a gel or membrane that arrays the nucleic acid molecules.

The invention further concerns the embodiment of such methods wherein the method additionally comprises incubating the sequestered nucleic acid molecules of two or more regions under conditions sufficient to permit the amplification of one or more preselected nucleic acid molecules if present at the regions, while preserving the positional relationship of the molecules relative to other molecules of the 2-dimensional array. The invention additionally concerns the embodiment of such methods wherein the method comprises incubating the sequestered nucleic acid molecules of all of the regions under conditions sufficient to permit the amplification of the one or more preselected nucleic acid molecules. The invention further concerns the embodiment of such methods wherein the method additionally comprises transferring the amplified nucleic acid species to two or more membranes, the membranes being differentially treated to enable the determination of the location(s) of amplified nucleic acid species. The invention further concerns the embodiment of such methods wherein the manipulation is selected from the group consisting of nucleic acid amplification, reverse transcription, labeling, cloning, and the assaying of a biomolecule. The invention further concerns the embodiment of such methods wherein one or more of the preselected nucleic acid molecule(s) are diagnostic of a disease state and/or wherein the nucleic acid molecules are amplified using a polymerase chain reaction.

The invention particularly concerns the embodiment of such methods wherein the molecular species are protein molecules. The invention further concerns the embodiment of such method wherein the cellular sample is an extract of a cell, and the 2-dimensional array is a gel or membrane that arrays the molecules of the extract. The invention further concerns the embodiment of such method wherein one or more of the protein molecule(s) are diagnostic of a disease state.

BRIEF DESCRIPTION OF THE FIGURES

FIG. 5 illustrates the use the use of the EMI apparatus of the present invention in combination with agarose gel spin transfer. Step 1: a sample is subjected to electrophoresis. Step 2: the electrophoresed gel is subjected to spin transfer of the separated nucleic acids onto the EMI apparatus of the present invention. Step 3: the individual wells of the EMI apparatus are then subjected to polymerase chain reaction amplification. Step 4: biomolecules are transferred from the microtiter wells through the LES membranes.

FIG. 6A: wells of a 384-well microtiter plate are indicated by circles. Open ovals indicate wells that were re-amplified. The position of the DNA band is visualized using ethidium bromide, and is indicated as a closed oval. FIG. 6B: samples were removed from the wells after spin transfer and re-amplified using the same HPV primers. The numbers indicate the well sample that was loaded into each lane, and then subjected to electrophoresis. Wells containing the desired band are marked with an arrow.

DESCRIPTION OF THE PREFERRED EMBODIMENTS

The invention concerns a method and apparatus for accomplishing and/or facilitating the analysis of multiple biomolecules arrayed in a two-dimensional (2D) array, such as a gel or other solid support.

Figure 1:
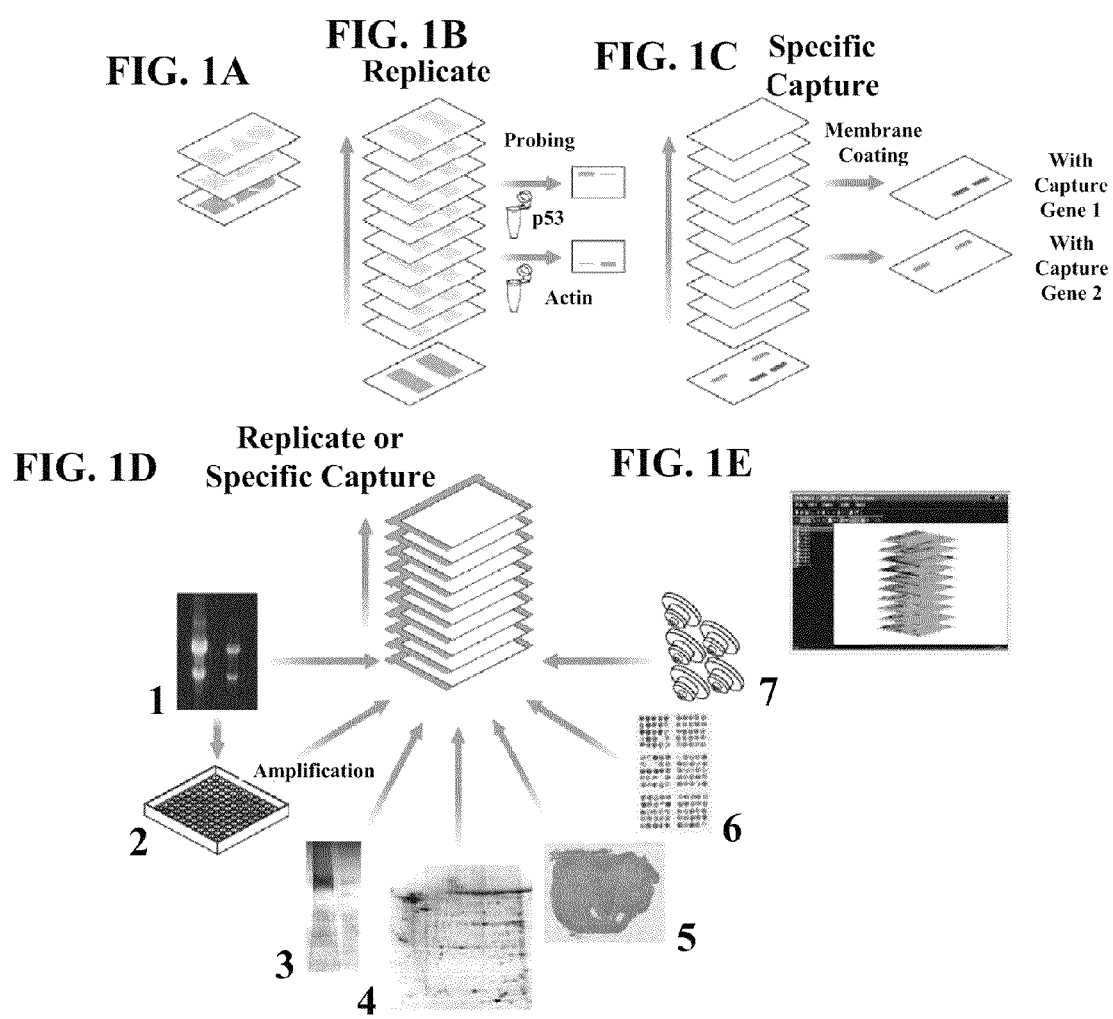
FIG. 1 is a schematic illustration of a preferred embodiment of the invention, and its use in layered expression scanning (LES). Panel A.: A biological sample is placed adjacent to a multilayered set of membranes. Panel B.: The specimen is transferred through the layers as an intact two-dimensional object. For the analysis step, LES can be used as either a closed or open system. In the open version, the membranes bind a subset of the target molecules, resulting in a series of 'replicate' membranes that can be subsequently probed for specific genes or proteins. In the closed version, desired molecules (e.g., specific antibodies or DNA molecules, etc.) are placed on each membrane. The biological sample is pre-labeled and passed through the layers. Panel C.: Desired molecules (e.g., proteins, mRNAs, etc.) are captured by their corresponding membrane and the expression level of each is measured. In this application, the membranes permit non-target molecules to pass through unimpeded; thus the closed system can be used with a large number (100 or more) of layers. Panel D.: Illustration of the use of LES in an automated or user-directed manner to allow comprehensive study of bio-samples in an automated fashion. An External Movement Inhibitor device (EMI) is employed to facilitate the amplification and/or other analysis of biomolecules arrayed on a gel, tissue sample, membrane, etc. LES software allows investigators to move seamlessly through the data sets, facilitating comparison of expression levels of multiple biomolecules in different cell population, regions, etc.

The invention is particularly suited for use in Layered Expression Scanning (LES). LES is a new technology co-developed by the National Institutes of Health and 20/20 GeneSystems, Inc. (Englert, C. R. et al. (2000) "LAYERED EXPRESSION SCANNING: RAPID MOLECULAR PROFILING OF TUMOR SAMPLES," *Cancer Res.* 60: 1526-1530). The method utilizes a layered array of membranes for molecular analysis and can be applied to a variety of life science platforms, including tissue sections, cells in culture, electrophoresis gels, multi-well plates, and tissue arrays (FIG. 1). The technique is preferably performed by passing the sample through the series of membrane layers while maintaining two-dimensional architecture, thus permitting the concurrent measurement of different RNA transcripts or proteins in each of the individual sample elements (e.g., various cellular phenotypes in a tissue section, bands on a gel, individual wells of a microtiter plate). The method has a number of properties that increase its utility. It is conceptually simple, requires no moving parts, can be used as an open or closed format, and maintains target biomolecules at a high concentration during the analysis process to produce sensitive measurements.

In preferred embodiments, the invention employs a separator, referred to herein as an External Movement Inhibitor device ("EMI") that can be imposed upon a two-dimensional solid array to isolate and sequester those biomolecules located at one region of the array from those biomolecules located at a different region of the array. Since the EMI sequesters the various molecular species, the architecture of the 2-dimensional pattern, and the spatial relationships of the molecules in the array are preserved.

The biomolecules of relevance to the present invention may be nucleic acid molecules (RNA, or DNA), proteins (enzymes, immunoglobulins, receptors, receptor ligands, hormones, antigens, etc.), carbohydrates or lipids. By isolating and sequestering the biomolecules of the array into discrete regions, the invention permits the analysis of some or all of such regions, so as to permit the detection of classes of molecules (e.g., nucleic acid molecules, proteins, etc.), and/ or specific molecules (e.g., DNA/RNA molecules of interest (for example those associated with the presence of a pathogen, or a tumor marker or receptor, etc.), or specific proteins (enzymes, cellular factors, receptors and receptor ligands, tumor markers, etc.), carbohydrates, metals, reporter molecules, etc.) that may be present in such regions.

Such analysis may optionally be conducted multiple times to thereby permit the detection of molecules in multiple sequestered regions. In a preferred embodiment, for example, a plurality of regions, and more preferably, all regions, sequestered by the EMI will be simultaneously evaluated for the desired molecules. In a preferred embodiment of the invention, such analysis will be performed on a series of replicated samples, so as to permit multiple evaluations to be accomplished, each investigating the presence of different molecules and/or different classes of molecules for some, most, and more preferably, all of the sequestered regions.

The same or different analyses can be conducted at different times in order to examine the change in concentration, state or nature of particular biomolecules over time at a particular sequestered region of the array, or at multiple sequestered regions.

The two-dimensional arrays of relevance to the present invention may be any of a wide variety of solid supports. Such supports particularly include "1-dimensional" gels (especially polyacrylamide gels, agarose gels, etc.), such as those typically employed to assess molecular weight, and "2-dimensional" gels, such as those employed to simultaneously separate analytes based on molecular size and charge. Other preferred supports include membranes (such as paper, nitrocellulose, etc.). Nitrocellulose membranes sold by 20/20 GeneSystems, Inc. (Rockville, Md.) are particularly preferred supports. The supports that may be used in accordance with the present invention also include tissue specimens, biopsies, etc.

Preferably, the EMI devices of the present invention will have a substantial number of grids, or wells, so as to be able to sequester the molecules of the array into a substantial number of regions. The devices are preferably suitable for sequestering the molecules present in closely positioned regions of the array so as to allow for nucleic acid/protein manipulation (amplification, reverse transcription, labeling, cloning, assaying of biomolecules, etc.) while maintaining the two-dimensional spatial orientation of the molecules of the array. Preferably, such number of grids, or wells will be greater than 50, more preferably, greater than 100, still more preferably, greater than 300, or greater than 1000. Preferred EMI devices include 96, 384, and 1536 well microtiter dishes.

Figure 2:
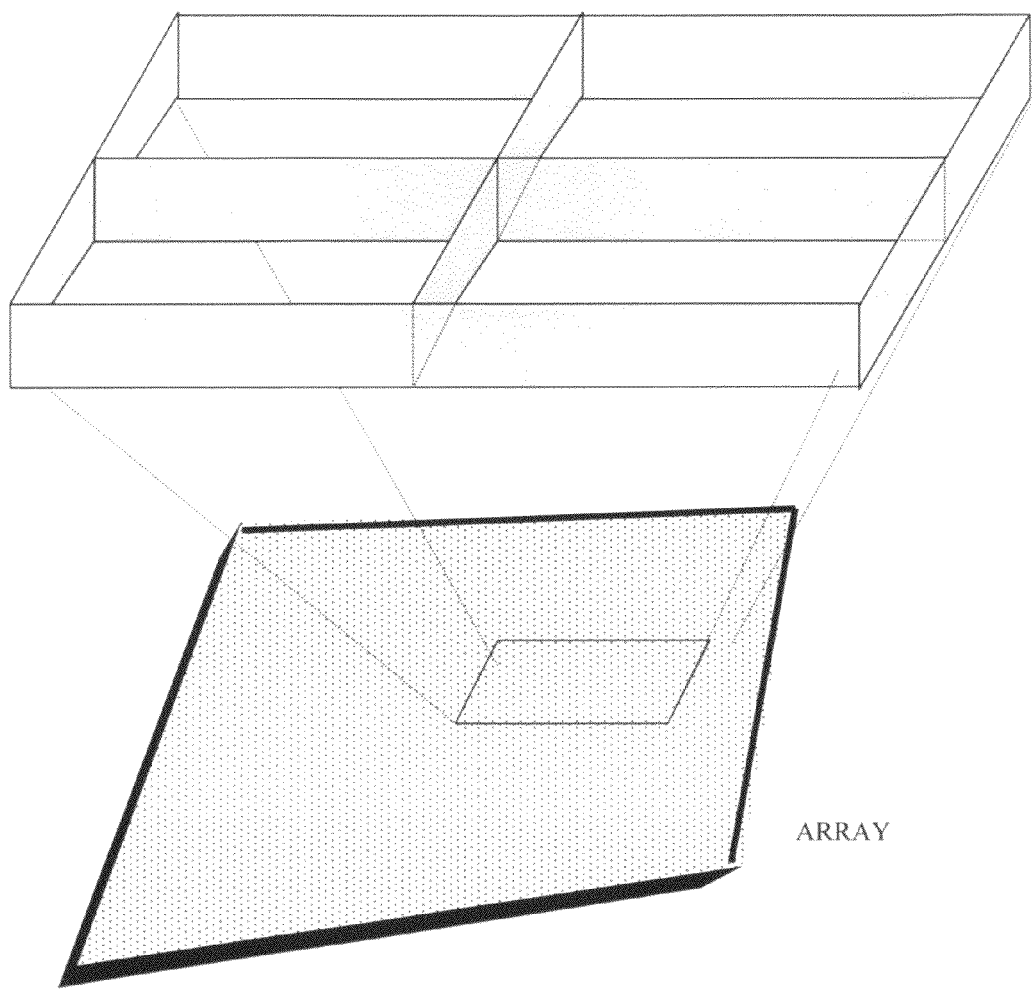
FIG. 2 illustrates an "open end" embodiment of the EMI apparatus of the present invention.
Figure 3:
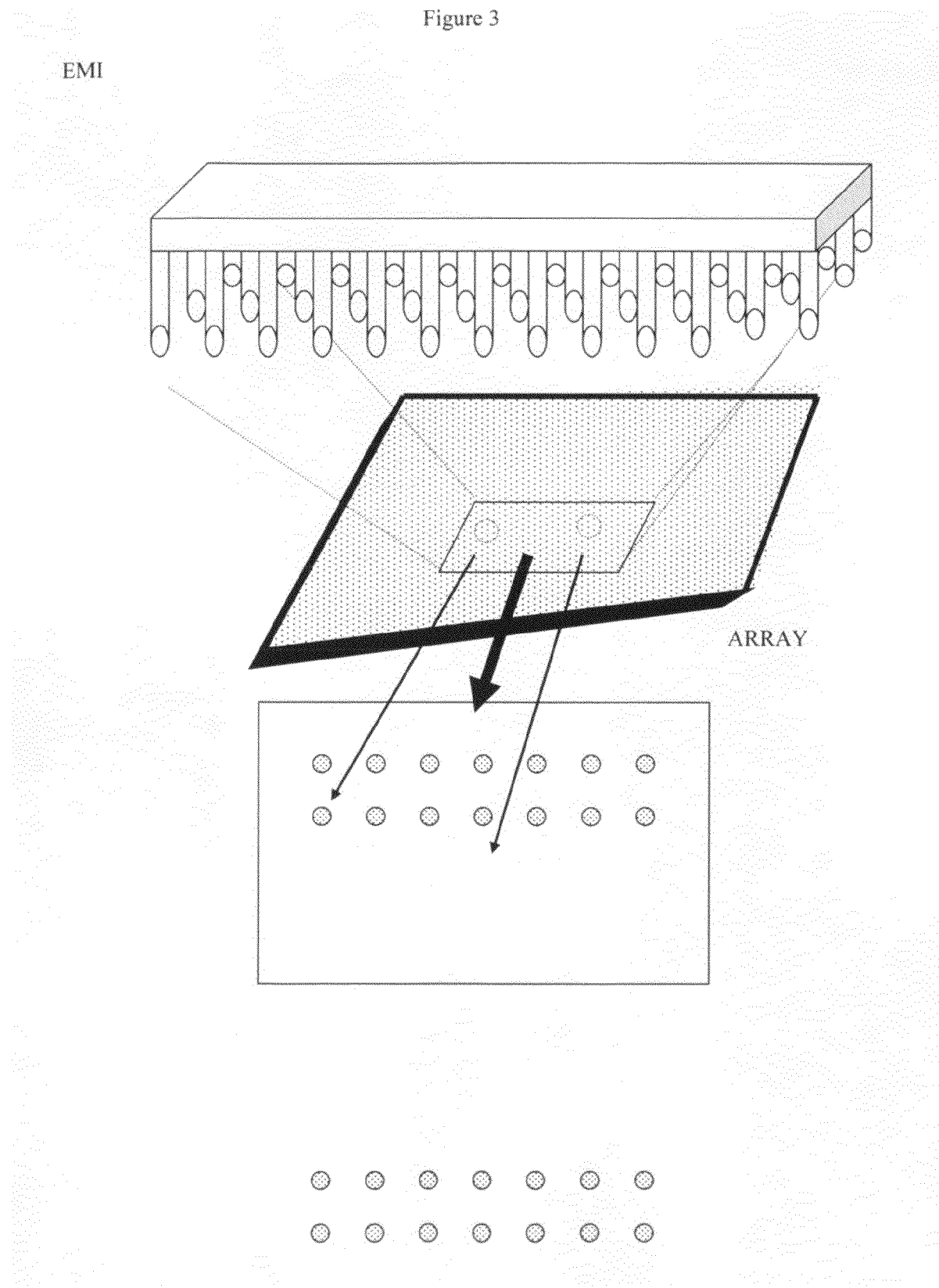
FIG. 3 illustrates a sampling needle embodiment of the EMI apparatus of the present invention.
Figure 4:
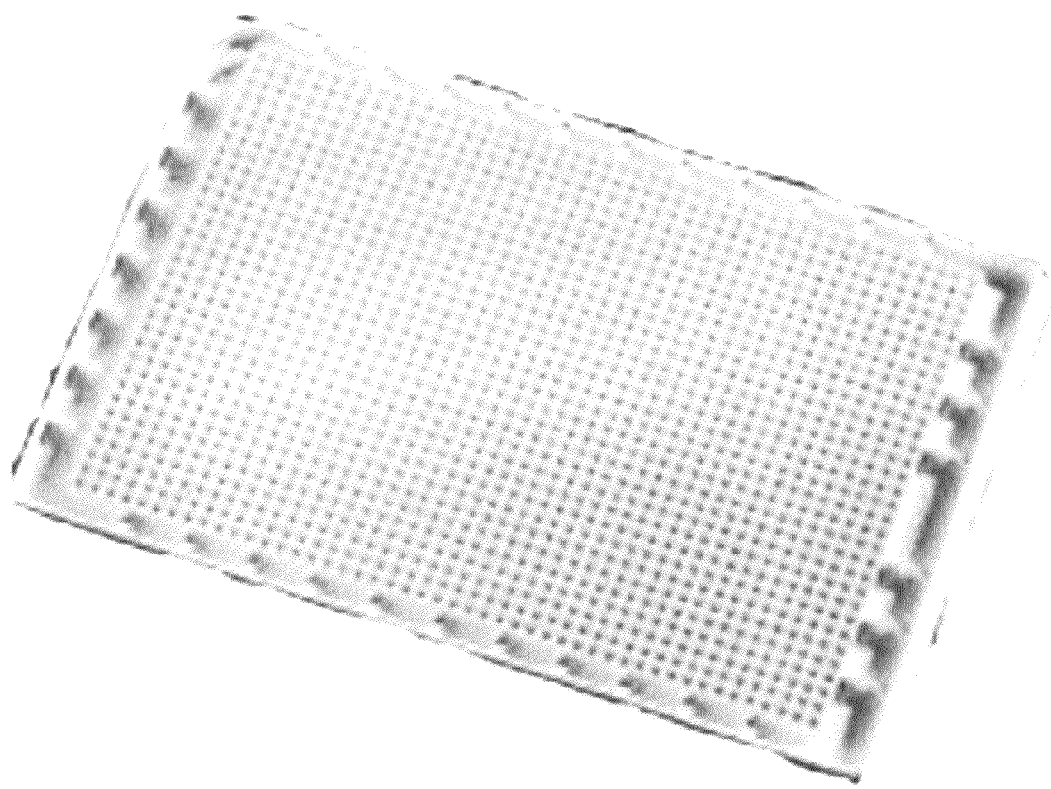
FIG. 4 illustrates a closed end "well" embodiment of the EMI apparatus of the present invention.

In one embodiment, the EMI may comprise a grid that is open on both top and bottom (FIG. 2), and can be used as a "punch" to sequester the biomolecules present in different regions of the array, which can then be analyzed in situ, or removed from the array (as by aspiration, inoculation, etc.) and subsequently analyzed. In an alternative embodiment (FIG. 3), the EMI may comprise a plurality of probes that may be hollow or solid, and that may be used to sample the biomolecules present in different regions of the array. In a preferred sub-embodiment of this embodiment of the invention, the probes or needles are first placed into contact with the array, and then contacted with a filter, gel, or other 2-dimensional surface that can be assayed for desired biomolecules. In a further embodiment (FIG. 4), the EMI may comprise a "partially closed" grid, such that when interposed into the array, the biomolecules of the array regions are captured into chambers or "wells." Conventional microtiter plates, for example may be employed for such use.

Having now generally described the invention, the same will be more readily understood through reference to the following examples, which are provided by way of illustration, and are not intended to be limiting of the present invention, unless specified.

EXAMPLE 1

EMI Devices

In one example of the invention, RNA transcripts of a biological sample are analyzed via gel electrophoresis to separate the transcripts by size, and the gel is then placed adjacent to an EMI and the entire complement of RNA is transferred into the wells. The EMI's grid causes each transcript to migrate directly into a well at precisely its position in the gel. By placing the EMI into a thermocycler, RT-PCR can be simultaneously performed on all of the transcripts (each localized in their own well), thereby significantly increasing the number of cDNAs corresponding to each mRNA. Significantly, such a process will lead to the amplification (and detection) of all transcripts, even those of low abundance. The EMI containing the amplified cDNAs may be analyzed by standard layered expression scanning (LES) analysis by transferring them to a stack of LES membranes.

The net effect of using the EMI in this example is to dramatically increase the nucleic acid content such that more replicate LES membranes can be produced, and/or, more sensitive measurements can be made, including low abundance transcripts that are not easily measurable on a standard northern blot (i.e., without an amplification step). Similar experiments could be carried out for DNA sample using Southern blots.

EXAMPLE 2

Direct Cell Target Analysis (DCTA)

A second application of the EMI devices of the present invention involves using an EMI device to facilitate Direct Cell Target Analysis (DCTA). In this method, a DCTA polymer is employed to target specific cells in a tissue section, and then all of the cellular material is transferred into an EMI. Since such transfer would maintain the section's 2-dimensional architecture, each well would contain the cellular proteins corresponding to specific regions/cells of the tissue section. The wells that contain the targeted cells would also contain the DCTA polymer (which could be attached to a labeling enzyme, e.g., lactoperoxidase, etc. to label proteins with $I^{125}$). The labeling reaction could then be carried out simultaneously in all of the wells of the EMI. Using the EMI device in this manner would facilitate the DCTA labeling reaction by providing a soluble environment, thereby permitting efficient and complete protein labeling to occur. Similar experiments could be carried out using reverse transcriptase (in place of lactoperoxidase) to produce labeled first-strand cDNA for microarray experiments.

EXAMPLE 3

Multiplex Analysis of RNA and Protein Gels Using Layered Expression Scanning

To specifically facilitate multiplex analysis of RNA and protein electrophoresis gels using layered expression scanning as an open system, a unique, highly efficient hybridization membrane was developed that permits ten blots to be produced from a single gel. Each blot can be subsequently probed for individual transcripts or proteins using standard procedures. The method increases the throughput rate of northern and immuno blots and importantly, permits an increase in the number of molecular measurements that can be made per biosample. The described technique makes feasible quantitative determination of the expression level of a large set of genes and proteins, such as those typically identified in array and proteomic studies. To assess the technical capabilities of the new membrane system, the following performance parameters were evaluated: hybridization characteristics, signal sensitivity, and reproducibility relative to standard blots.

Multiplex Northern Blots Hybridization and/or total RNA binding characteristics of the layered array membranes were assessed in several experiments as follows. Total RNA (15-30 µg) from cell lines MDA-MB-453 (Geneka Biotechnology Inc, Montreal Quebec), Jurkat (Geneka Biotechnology Inc, Montreal Quebec), HeLa (Ambion Inc, Austin Tex.), Osteosarcoma MG-63 (Ambion Inc, Austin Tex.) was electrophoresed in a 1%, denaturing agarose gel. After washing the gel twice for five minutes in DEPC-treated water, a standard northern blot capillary transfer was performed overnight, except that the ten-layer membrane system (20/20 GeneSystems) was substituted for a nitrocellulose membrane. The following setup was utilized (from bottom to top): 20×SSC transfer buffer, transfer paper (Gel Blot Paper, Schleicher & Schuell, Keene, N.H.), agarose gel, 10-layer membrane set (20/20 GeneSystems, Rockville, Md.), one nitrocellulose membrane (Protran, Schleicher & Schuell, Keene, N.H.), 20-40 pieces of transfer paper (Gel Blot Paper, Schleicher & Schuell, Keene, N.H.), and a standardized weight (7 g/cm$^2$). After transfer, the membranes were UV-crosslinked (1,200 mJ), and total RNA capture was assessed by SYBR DX DNA Blot Stain (Molecular Probes, Eugene, Oreg.). For experiments to analyze specific gene levels, the membranes were pre-hybridized in 6×SSC, 0.5% SDS, 10 µg/ml salmon sperm, and 5×Denhardt's, at 55° C. for 30 min. Twenty-five to 50 ng of each probe was random-prime labeled using the Rediprime II Kit (Amersham Pharmacia Biotech, Buckinghamshire, England) and 33p incorporation. The membranes were hybridized using 2,000-10,000 cpm/µl, at 55° C. in a rotating tube overnight, and then washed two times for 10 minutes in 1×SSC 0.5% SDS, and two times for 10 minutes in 1×SSC, 0.1% SDS, and exposed using the Phosphorimager 445 SI (Microdinamic Engineering, Rockville Md.). Quantitation of signals was performed using ImageQuant software (IQMac v1.2). A set of parallel experiments was also performed under identical conditions, but the stack often layered membranes was replaced with a conventional nitrocellulose membrane (Protran, Schleicher & Schuell, Keene, N.H.). Stripping of layered membranes was performed in a boiling solution of 0.5% SDS for 5-10 min, and membranes were subsequently re-hybridized.

Multiplex Immuno Blots Generation of multiple protein blots was first assessed by evaluating total protein staining on ten blots. Protein extract was obtained by lysing Jurkat cells in PBS with 1 SDS. The concentration of protein was determined by using the BCA Protein Assay Reagent Kit (Pierce, Rockford, Ill.). Twenty µg and 40 µg of cellular protein extract, and 10 µg of bovine serum albumin (ICN) was separated by polyacrylamide gel electrophoresis (PAGE) on a 10% TRIS/HCl gel (BioRad, Hercules, Calif.). Transfer from the gel onto ten membranes (20/20 GeneSystems, Rockville, Md.) was done using the BioMax MultiBlot Kit for Proteins (Kodak, Rochester, N.Y.) according to the manufacturer's recommendation. After transfer, membranes were rinsed in double distilled water and stained with the FastBLUE Staining Kit (Chemicon, Temecula, Calif.). Stained membranes were digitized by scanning on UMAX Vista Scan (UMAX Technologies Inc, Dallas, Tex.) and the image was stored in TIFF format. Quantitation of staining intensity was performed by Kodak ID software (Kodak, Rochester, N.Y.).

To evaluate total and activated levels of Raf and Erk proteins, cellular extracts were made in PBS with 1% SDS from the following cell lines: HaCat, Jurkat, HeLa, NIH3T3, SvV480, MCF7, 293T, and S49. Twenty µg of protein extract was loaded per lane. Samples were separated by PAGE on a 10% TRIS/HCl gel (BioRad, Hercules, Calif.) and transferred onto ten membranes (20/20 Gene Systems, Rockville, Md.) using the BioMax MultiBlot Kit for Proteins (Kodak, Rochester, N.Y.) according to the manufacturer's recommendation. After transfer, membranes were rinsed in TBS buffer (50 mM TRIS pH 8.0, 150 mM NaCl, 0.01% Tween-20) and blocked in 1× casein solution (Vector Laboratories, Burlingame, Calif.) for 15 min. Membranes were then incubated for 8 hours at 40° C. in a 1:500 dilution of anti-Raf antibody (Transduction Laboratories, Palo Alto, Calif.), or in a 1:500 dilution of anti-phospho-Raf (Cell Signaling, Beverly, Calif.), or in a 1:1000 dilution of anti-Erk antibody (Santa Cruz Biotechnologies, Santa Cruz, Calif.), or in a 1:500 dilution of anti-phospho Erk antibody (Cell Signaling, Beverly Calif.). After incubation, the membranes were washed in TBS buffer and incubated in a 1:2000 dilution of appropriate secondary antibody conjugated to HRP (Amersham-Pharmacia, Piscataway, N.J.). Proteins were visualized with ECL Plus reagent (Amersham-Pharmacia, Piscataway, N.J.) and the images captured on Kodak Image Station CF440 (Kodak, Rochester, N.Y.). After primary incubation with the antibody of interest, all of the membranes were incubated in a 1:1000 dilution of anti-GAPDH antibody (Chemicon, Temecula, Calif.) to confirm equal loading and transfer from the gel.

The membranes were found to perform similarly for both RNA and protein applications. The quantity and size distribution of RNA that is captured by each of the membranes in the system was determined by transferring 15 µg of total RNA from MDA-MB-453 cells through the layers. A typical rRNA pattern with both 28S and 18S bands is observed, indicating that the low binding capacity of the membranes results in rapid saturation during the transfer process, thus permitting the majority of the sample to progress through and bind to subsequent membranes. The maximal variability was found to be in membrane #1, which showed a 32% increase over the average signal, and in membrane #4 which showed a 23% decrease. This degree of alteration has minimal effect on subsequent probe hybridization results, and is within the normal range of experiment-to-experiment variability typically observed with standard northern blots. Similar results were obtained using protein gels. The difference in intensity signal for all 10 membranes ranged from 12-22% from the average value.

The hybridization characteristics of the system were evaluated by analyzing the signal generated by a GAPDH probe on each of ten membranes using 15 µg of total RNA from the osteosarcoma cell line MG-63. A specific 1.3 kb band corresponding to the GAPDH transcript is seen in each membrane. Similar to overall RNA levels, only a relatively small variation in detected signal was observed between the membranes (ranging from a 41% decrease from the average to a 29% increase). Taken together, the total RNA, protein and GAPDH quantitation data demonstrate that the layered array system generates ten membranes that reliably bind RNA and protein, and can be successfully probed for specific genes.

In addition to its low capacity binding characteristics, the new membrane was designed to provide increased hybridization efficiency. Even though it binds significantly less RNA or protein than other membranes, the signal intensity after probing approaches that obtained in a traditional blot. This feature significantly expands the utility of the system, as investigators can perform multiple northern or immuno blots from a single sample preparation, each with a high degree of sensitivity. To compare hybridization results between the layered array system and a standard blot, 15 µg of total osteosarcoma MG-63 cell line RNA was analyzed by both LES and traditional methods in parallel. After the transfer of RNA out of the gels, all membranes were probed, washed, and imaged under identical conditions. Qualitatively, the results obtained were similar between the two blots in terms of specificity and hybridization background. Densitometric analysis indicated the GAPDH band on the new membrane had a signal equal to 90% of the nitrocellulose membrane. In general, the layered array membranes are observed to produce band intensities ranging from 60-95% of traditional blots for both mRNA and proteins. The subset of membranes that show 40% less intensity have a minimal effect on the utility of the system; however, it is desirable in some experiments to expose the blots to autoradiography film for an extended period of time in order to produce band patterns that are identical to those seen on traditional blots.

The ability to perform multiple expression measurements on the same sample preparation has significant utility for investigators. For example, different members of a signaling pathway can be simultaneously measured, including both total protein and the subset of activated protein. This aspect of the invention is illustrated by the following experiment. Total protein lysate from eight cell lines was separated by gel electrophoresis and ten blots were subsequently produced in a single transfer. Membranes 3-6 were analyzed for total Raf protein, phosphorylated Raf, total Erk protein, and phosphorylated Erk, respectively. It is found that the ratio of total to activated protein varies among the cell lines, indicating that protein expression and activation status are independently regulated. Thus, measuring both forms of Raf and Erk proteins is important to an understanding of the overall kinetics and activation state of the pathway. Multiplex measurements such as these are likely to become increasingly important in the future as investigators move toward a systems-based understanding of biological processes.

To assess the uniformity and reproducibility of the layered array system, 20 µg of HeLa cell line total RNA was analyzed in triplicate using GAPDH, HPV-18 E6/E7, PCNA, and cdc2 probes. The selected target genes are present in HeLa cells at varying levels of abundance, thus the membranes could be evaluated across a 20-fold range of expression. The signals for each lane were quantified and compared. The intra-membrane lane variability ranged from a 29% increase from the average to a 19% decrease, with a median variance of ±9.3%. These results were then compared with the membrane variability of traditional northern blots using nitrocellulose membranes. Twenty µg of HeLa cell line total RNA was run on three separate electrophoresis gels and subsequently blotted onto nitrocellulose. The first blot was probed with HPV18 E6/E7, the second with PCNA, and the third with cdc2. The signal intensity was found to vary among the lanes from a 42% percent increase from the average to a 24% decrease, with a median variance of 13.6%.

The inter-membrane levels of total RNA staining on the three standard northern blots was also examined, and compared it with data from the layered array membranes. The inter-membrane total RNA levels among the three standard northern blots were found to vary among the lanes from a 42% percent increase from the average, to a 58% decrease. Therefore, based on both total RNA content and probe hybridization data, the layered membrane array system was found to perform similarly to standard northern blots in terms of intra- and inter-blot reproducibility.

The ability of the layered array system to reliably detect relatively small differences (2-3 fold) in gene expression levels was evaluated, and compared the data with that from a traditional blot. Thirty µg of total RNA from Jurkat and MDA-MB-453 cell lines were separated on an agarose gel and transferred to a stack of ten membranes. PCNA probe was hybridized to membranes 2, 3, 5, 7, and 9, and GAPDH probe was hybridized to membrane 4. Relative PCNA expression between the two cell types was calculated using GAPDH levels to normalize the amount of RNA loaded on the gel. Each of the five membranes probed for PCNA showed higher levels of expression in the Jurkat cells, ranging from a 1.28- to a 2.69-fold difference. To compare these results with standard northern blots, two 30 µg aliquots of Jurkat and MDA-MB-453 RNA were electrophoresed and subsequently transferred to two separate nitrocellulose membranes. Both blots were probed for PCNA and the band intensities were normalized using total RNA levels in the gel. Both blots showed higher levels of PCNA expression in Jurkat compared to MDA-MB-453 cells. Blot #1 showed a 1.56 fold difference and blot #2 showed a 3.76 fold difference. Overall, the data indicate that both layered membrane arrays and standard northern blots can detect expression level changes at the 2-3 fold level, and show similar ranges of blot-to-blot variation.

The experiment was designed to emulate standard experimental approaches utilized in the laboratory so that a realistic comparison between the two methods could be made. For the layered array system, one typically probes one membrane for a housekeeping gene to normalize gel loading, and then performs expression measurements of additional transcripts or proteins on the remaining layers. As a practical matter, this is an optimal use of the system and allows data to be generated quickly and efficiently. For standard northern blots, investigators often normalize gel loading using total RNA levels in the gel and this is the method employed in the experiment described above. Alternatively, one can simultaneously probe a blot against a gene of interest and a housekeeping gene (if they are of different sizes), or one can probe for the gene of interest, strip the blot, and re-probe for a housekeeping gene. The layered array system was compared with standard northern blots using each of these approaches. In each instance, the layered membrane system performed as well as standard northern blots in accurately measuring transcript levels.

The utility of standard northern and immuno blots can be increased by stripping and reprobing them. While this approach is useful, it has significant limitations. The stripping procedure for both protein and RNA blots is harsh, typically resulting in decreased hybridization levels and increased background each time the blot is probed. Anomalous results are occasionally observed after this procedure. Such results may be due to damage to the blot and/or, alterations in hybridization characteristics of a subset of target molecules. Nevertheless, the ability to re-probe blots can be useful in many experiments. Therefore, this procedure was evaluated for the new layered membrane system using actin and GAPDH probes (as model probes). Although this procedure can be applied successfully to the layered membranes, a decrease in membrane performance was observed after the stripping procedure, similar to that seen with traditional blots. For many experiments, it is found that the use of the membrane array system eliminates the need for re-probing of blots.

The layered membrane technique described herein offers several key advantages. It is easy to perform, relies on well-established probe and antibody hybridization methods, is an open system that permits investigators to analyze any gene or protein of interest, and provides information beyond simple expression levels such as transcript size(s) and protein processing status. A particularly important technical aspect of the method is that all of the blots are produced from a single sample, analyzed on one gel. This feature eliminates a number of potential experimental artifacts including: variance in sample preparation and solubility in loading buffer, problems associated with sample storage and/or freezing-thawing, and the typical variability seen among electrophoretic gel runs.

Utilization of the multi-blot application of layered expression scanning can augment experimental strategies in the laboratory. For example, quantitative follow-up measurement of a large set of genes identified in cDNA micro array experiments can be performed on a set of samples in a rapid and relatively low-cost fashion. Moreover, investigators can quickly extend their study from a single transcript or protein of interest to related genes in a family and/or proteins involved in an associated biochemical pathway. Even when investigators do not initially need to perform ten separate measurements, it is advantageous to store the membranes for future experiments.

The layered array system has been shown to be robust and reliable. The method permits investigators to produce usable blots from each RNA or protein gel, thus significantly increasing their utility.

The EMI devices described of the invention may significantly extend the future capabilities of LES technology. As an example, EMI devices may be employed to add an amplification step (e.g., PCR, etc.) to the RNA gel or tissue application. The amplification is performed on the entire transcriptome, after the mRNA has been separated by gel electrophoresis, but prior to transfer through the membrane layers, using a method similar to in-situ PCR of a tissue section. This approach will increase the sensitivity level of each blot, as well as the number of blots that can be created per gel. Moreover, PCR-based layered array membranes may permit multiplex, hybridization-based analysis of developmental biology or micro-dissected cell samples that typically do not produce enough RNA for standard blotting techniques. Thus, the LES layered membrane array methodology has immediate utility for multiplex mRNA and protein expression measurements, particularly in combination with an EMI device.

EXAMPLE 4

Microarrays: Post-Analysis Follow-Up and Validation

Two important questions for investigators to consider when evaluating microarray expression data: are whether the results are valid (i.e., accurate) for the specific biological system under study, and whether the data fundamentally describe the phenomenon being investigated.

Obtaining valid expression measurements may involve more than just post-array verification of results using an independent laboratory approach. Introduction of artifact is possible at any time during an array experiment, thus each component of the procedure is to be carefully considered. Overall, the validation process may be divided into three areas: experimental quality control, independent confirmation of data, and universality of results.

Microarray Experiment Quality Control Optimizing array experiments at the front-end decreases the time and effort required to subsequently invalidate erroneous expression results. Briefly, the following parameters may significantly affect the accuracy of array experiments. Of significant importance in eliminating "noise" in the data are repeat experiments. Multiple arrays should be performed, including replicates of each RNA sample, as well as with independent RNA preparations. Additionally, "up-front validation" can be performed by including separate regions of each gene on the array. This allows for multiple measurements of expression as part of the initial experiment. An important step that affects the validity of the downstream data is image acquisition. There are several commercial software packages available, in addition to programs provided online at no cost to investigators. Factors that can affect results include the methods for normalization and background subtraction, data processing and standardization, and use of visualization tools (Brazma, A. et al. (2001) "MINIMUM INFORMATION ABOUT A MICRO ARRAY EXPERIMENT (MIAME)-TOWARD STANDARDS FOR MICRO ARRAY DATA," Nat. Genet. 29:365-371).

Selecting statistical approaches can be problematic due to the large number of analysis systems available. The micro array field is rapidly evolving, and the number of publications on methods is substantial (Hess, K. R. et al. (2001) "MICROARRAYS: HANDLING THE DELUGE OF DATA AND EXTRACTING RELIABLE INFORMATION," *Trends in Biotech.* 19:463-468; Pan, W. (2002) "A COMPARATIVE REVIEW OF STATISTICAL METHODS FOR DISCOVERING DIFFERENTIALLY EXPRESSED GENES IN REPLICATED MICRO ARRAY EXPERIMENTS," *Bioinformatics* 18:546-554; Nadon, R. et al. (2002) "STATISTICAL ISSUES WITH MICROARRAYS: PROCESSING AND ANALYSIS," *Trends in Genet.* 18:265-271). To date, there is no consensus approach to statistical analysis and thus array results are analyzed in a variety of different ways. However, at a minimum, there are basic methods that may be applied. Numerical management of the data permits removal of artifacts caused by low gene expression and low ratios (for brief review, see Mills, J. C. et al. (2001) "MICROARRAYS AND BEYOND: COMPLETING; THE JOURNEY FROM TISSUE To CELL," *Nat. Cell Biol.* 3:175-178). Following data pre-processing and numerical management, a statistical approach must be chosen to determine gene significance (as an example, see Mutch, D. M. et al. (2001) "MICROARRAY DATA ANALYSIS: A PRACTICAL APPROACH FOR SELECTING DIFFERENTIALLY EXPRESSED GENES," *Genome Biol.* 2, preprint 0009) Finally, high-end computational analysis may be employed such as clustering, multidimensional scaling, or pattern identification, including neural networks and heuristic algorithms (Ellis, M. et al. (2001) "DEVELOPMENT AND VALIDATION OF A METHOD FOR USING BREAST CORE NEEDLE BIOPSIES FOR GENE EXPRESSION MICRO ARRAY ANALYSES," *Clin. Cancer Res.* 8:1155-1166). The goal of all of these efforts is accurate identification of differences in gene expression between the sample sets, and maximal use of the information toward a better understanding of the biological process(es) under study.

Independent Confirmation of Results There are two approaches to independent confirmation of micro array data; in silica analysis, and laboratory-based analysis. The in silica method utilizes a comparison of array results with information available in the literature, as well as public or private expression databases, and provides the opportunity to validate data without further experimentation. For example, multiple studies of prostate cancer profiling have been published (Luo, J. et al. (2001) "HUMAN PROSTATE CANCER AND BENIGN PROSTATIC HYPERPLASIA: MOLECULAR DISSECTION BY GENE EXPRESSION PROFILING," *Cancer Res.* 61:4683-4688; Welsh, J. B. et al. (2001) "ANALYSIS OF GENE EXPRESSION IDENTIFIES CANDIDATE MARKERS AND PHARMACOLOGICAL TARGETS IN PROSTATE CANCER," *Cancer Res.* 61:5974-5978; LaTulippe, E. et al. (2002) "COMPREHENSIVE GENE EXPRESSION ANALYSIS OF PROSTATE CANCER REVEALS DISTINCT TRANSCRIPTIONAL PROGRAMS ASSOCIATED WITH METASTATIC DISEASE," *Cancer Res.* 62:4499-4506; Dhanasekaran, S. M. et al. (2001) "DELINEATION OF PROGNOSTIC BIOMARKERS IN PROSTATE CANCER," *Nature* 412:822-826; Emmert-Buck, M. R et al. (2000) "MOLECULAR PROFILING OF CLINICAL TISSUE SPECIMENS: FEASIBILITY AND APPLICATIONS," *Am. J. of Pathol.* 156:1109-1115; Magee, J. A. et al. (2001) "EXPRESSION PROFILING REVEALS HEPSIN OVEREXPRESSION IN PROSTATE CANCER," *Cancer Res.* 61:5692-5696; Stamey, T. A. et al. (2001) "MOLECULAR GENETIC PROFILING OF GLEASON GRADE 4/5 PROSTATE CANCERS COMPARED TO BENIGN PROSTATIC HYPERPLASIA," *J. Urol.* 166:2171-2177; Ahram, M. et al. (2001) "PROTEOMIC ANALYSIS OF HUMAN PROSTATE CANCER," *Mol. Carcin.* 33: 9-15; Singh, D. et al. (2002) "GENE EXPRESSION CORRELATES OF CLINICAL PROSTATE CANCER," *Cancer Cell* 1:203-209; Svaren, J. et al. (2000) "EGR1 TARGET GENES IN PROSTATE CARCINOMA CELLS IDENTIFIED BY MICROARRAY ANALYSIS," *J. Biol. Chem.* 275: 38524-38531; Chaib, H. et al. (2001) "PROFILING AND VERIFICATION OF GENE EXPRESSION PATTERNS IN NORMAL AND MALIGNANT HUMAN PROSTATE TISSUES BY cDNA MICROARRAY ANALYSIS," *Neoplasia* 3:43-52; Porkka, K. et al. (2002) "AMPLIFICATION AND OVEREXPRESSION OF ELONGIN C GENE DISCOVERED IN PROSTATE CANCER BY cDNA MICROARRAYS," *Lab. Invest.* 82:629-637; Mousses, S. et al. (2002) "CLINICAL VALIDATION OF CANDIDATE GENES ASSOCIATED WITH PROSTATE CANCER POGRESSION IN THE CWR22 MODEL SYSTEM USING TISSUE MICROARRAYS," *Cancer Res.* 62:1256-1260 (2002). In a meta-analysis of the data sets from four of these papers, several differentially expressed genes were found to be common to the majority of the studies, the serine protease hepsin as an example (Rhodes, D. et al. (2002) "META-ANALYSIS OF MICROARRAYS: INTERSTUDY VALIDATION OF GENE EXPRESSION PROFILES REVEALS PATHWAY DYSREGULATION IN PROSTATE CANCER," *Cancer Res.* 62:4427-4433). Moreover, some of these genes, such as glutathione-S-transferase, have previously been identified as aberrantly expressed in prostate cancer in studies using methods other than microarrays (Canada, A. T. et al. (1996) "GLUTATHIONE AND GLUTATHIONE S-TRANSFERASE IN BENIGN AND MALIGNANT PROSTATE CELL LINES AND PROSTATE TISSUES," *Biochem. Pharm.* 51:87-90). Agreement between array results from other groups, as well as with known expression information in the literature, validates the general performance of a system and provides confidence in the overall data, including the unique and novel discoveries made in a study. It is likely that the in silica approach to validation will become more useful when standardized methods for reporting array data, such as the MIAME format (Minimal Information About a Microarray Experiment) are uniformly applied (Brazma, A. et al. (2001) "MINIMUM INFORMATION ABOUT A MICRO ARRAY EXPERIMENT (MIAME)-TOWARD STANDARDS FOR MICRO ARRAY DATA," *Nat. Genet.* 29:365-371).

Laboratory-based data validation provides independent, experimental verification of gene expression levels, and typically begins with the same samples that were studied in the initial array experiment(s). The methodology employed varies depending upon the scientific question posed, but commonly used techniques involving mRNA include:

Semi-Quantitative RT-PCR and real-time RT-PCR (see, for example, Al Moustafa, A. E. et al. (2002) "IDENTIFICATION OF GENES ASSOCIATED WITH HEAD AND NECK CARCINOGENESIS BY cDNA MICROANAY COMPARISON BETWEEN MATCHED PRIMARY NORMAL EPITHELIAL AND SQUAMOUS CARCINOMA CELLS," *Oncogene* 21:2634-2640; Chaib, H. et al. (2001) "PROFILING AND VERIFICATION OF GENE EXPRESSION PATTERNS IN NORMAL AND MALIGNANT HUMAN PROSTATE TISSUES BY cDNA MICROARRAY ANALYSIS," *Neoplasia* 3:43-52; Luo, J. et al. (2001) "HUMAN PROSTATE CANCER AND BENIGN PROSTATIC HYPERPLASIA: MOLECULAR DISSECTION BY GENE EXPRESSION PROFILING," *Cancer Res.* 61:4683-4688; Luo, J. H. et al. (2002) "GENE EXPRESSION ANALYSIS OF PROSTATE CANCER," *Mol. Carcin.* 33:2535; Bangur, C. S. et al. (2002) "IDENTIFICATION OF GENES OVER-EXPRESSED IN SMALL CELL LUNG CARCINOMA USING SUPPRESSION SUBTRACTIVE HYBRIDIZATION AND cDNA MICROARRAY EXPRESSION ANALYSIS," *Oncogene* 21:3814-3825; Jiang, Y. et al. (2002) "DISCOVERY OF DIFFERENTIALLY EXPRESSED GENES IN HUMAN BREAST CANCER USING SUBTRACTED cDNA LIBRARIES AND cDNA MICROARRAYS," *Oncogene* 21:2270-2282; Alevizos, I. et al. (2001) "ORAL CANCER IN VIVO GENE EXPRESSION PROFILING ASSISTED BY LASER CAPTURE MICRODISSECTION AND MICROARRAY ANALYSIS," *Oncogene* 20:6196-6204; Scheidl, S. J. et al. (2002) "mRNA EXPRESSION PROFILING OF LASER MICROBEAM MICRODISSECTED CELLS FROM SLENDER EMBRYONIC STRUCTURES," *Amer. J. of Pathol.* 160:801-813; Svaren, J. et al. (2000) "EGR1 TARGET GENES IN PROSTATE CARCINOMA CELLS IDENTIFIED BY MICROARRAY ANALYSIS," *J. Biol. Chem.* 275:38524-38531);

Northern Analysis (see, for example, Taniguchi, M. et al. (2001) "QUANTITATIVE ASSESSMENT OF DNA MICROARRAYS—

Comparison With Northern Blot Analyses," *Genomics* 71:34-39; Clark, J. et al. (2002) "Identification Of Amplified And Expressed Genes In Breast Cancer By Comparative Hybridization Onto Micro Arrays Of Randomly Selected cDNA Clones," *Genes, Chrom. and Cancer* 34:104-114; Amundson, S. A. et al. (1999) "Fluorescent cDNA Microarray Hybridization Reveals Complexity And Heterogeneity Of Cellular Genotoxic Responses," *Oncogene* 18:3666-3672; Chaib, H. et al. (2001) "Profiling And Verification Of Gene Expression Patterns In Normal And Malignant Human Prostate Tissues By cDNA Microarray Analysis," *Neoplasia* 3:43-52; Dhanasekaran, S. M. et al. (2001) "Delineation Of Prognostic Biomarkers In Prostate Cancer," *Nature* 412:822-826);

Ribonuclease Protection Assay (Taniguchi, M. et al. (2001) "Quantitative Assessment Of DNA Microarrays—Comparison With Northern Blot Analyses," *Genomics* 71:34-39; Hodge, D. L. et al. (2002) "IL-2 And IL-12 Alter NK Cell Responsiveness To IFN-Gammainducible Protein 10 By Down-Regulating CXCR3 Expression," *J. Immunol.* 168:60906098; Saban, M. R. et al. (2001) "Time Course Of LPS-Induced Gene Expression In A Mouse Model Of Genitourinary Inflammation," *Physiol. Genomics* 5:147-160); and In Situ Hybridization (ISH) Or Immunohistochemistry (IHC) Using Tissue Microarrays (Bonaventure, P. et al. (2002) "Nuclei And Subnuclei Gene Expression Profiling In Mammalian Brain," *Brain Res.* 943:38-47; Qi, Z. Y. et al. (2002) "Isolation Of Novel Differentially Expressed Genes Related To Human Glioma Using cDNA Micro Array And Characterizations Of Two Novel Full-Length Genes," *J. Neurooncol.* 56:197-208; Porkka, K. et al. (2002) "Amplification And Overexpression Of Elongin C Gene Discovered In Prostate Cancer By cDNA Microarrays," *Lab. Invest.* 82:629-637; Mousses, S. et al. (2002) "Clinical Validation Of Candidate Genes Associated With Prostate Cancer Progression In The CWR22 Model System Using Tissue Microarrays," *Cancer Res.* 62:1256-1260). Commonly used techniques involving Proteins include immunoblots and immunohistochemistry (IHC) (Al Moustafa, A. E. et al. (2002) "Identification Of Genes Associated With Head And Neck Carcinogenesis By cDNA Microanay Comparison Between Matched Primary Normal Epithelial And Squamous Carcinoma Cells," *Oncogene* 21:2634-2640; Burton, G. R. et al. (2002) "Microarray Analysis Of Gene Expression During Early Adipocyte Differentiation," *Gene* 293:21-31) and/or IHC via tissue microarrays (Dhanasekaran, S. M. et al. (2001) "Delineation Of Prognostic Biomarkers In Prostate Cancer," *Nature* 412:822-826; Mousses, S. et al. (2002) "Clinical Validation Of Candidate Genes Associated With Prostate Cancer Progression In The CWR22 Model System Using Tissue Microarrays," *Cancer Res.* 62:1256-1260).

Commonly used methods involving proteins include:

Immunoblot Al Moustafa, A. E. et al. (2002) "Identification Of Genes Associated With Head And Neck Carcinogenesis By cDNA Microanay Comparison Between Matched Primary Normal Epithelial And Squamous Carcinoma Cells," *Oncogene* 21:2634-2640; Burton, G. R. et al. (2002) "Microarray Analysis Of Gene Expression During Early Adipocyte Differentiation," *Gene* 293:21-31; and Immunohistochemistry (IHC) and/or IHC via tissue microarrays Dhanasekaran, S. M. et al. (2001) "Delineation Of Prognostic Biomarkers In Prostate Cancer," *Nature* 412:822-826; Mousses, S. et al. (2002) "Clinical Validation Of Candidate Genes Associated With Prostate Cancer Progression In The CWR22 Model System Using Tissue Microarrays," *Cancer Res.* 62:1256-1260 (2002).

See, in particular, Luo, J. et al. (2001) "Human Prostate Cancer And Benign Prostatic Hyperplasia: Molecular Dissection By Gene Expression Profiling," *Cancer Res.* 61:4683-4688; Dhanasekaran, S. M. et al. (2001) "Delineation Of Prognostic Biomarkers In Prostate Cancer," *Nature* 412:822-826; Stamey, T. A. et al. (2001) "Molecular Genetic Profiling Of Gleason Grade 4/5 Prostate Cancers Compared To Benign Prostatic Hyperplasia," *J. Urol.* 166:2171-2177; Singh, D. et al. (2002) "Gene Expression Correlates Of Clinical Prostate Cancer," *Cancer Cell* 1:203-209; Al Moustafa, A. E. et al. (2002) "Identification Of genes associated With Head And Neck Carcinogenesis By cDNA Microanay Comparison Between Matched Primary Normal Epithelial And Squamous Carcinoma Cells," *Oncogene* 21:2634-2640; Bangur, C. S. et al. (2002) "Identification Of Genes Over-Expressed In Small Cell Lung Carcinoma Using Suppression Subtractive Hybridization And cDNA Microarray Expression Analysis," *Oncogene* 21:3814-3825; Alevizos, I. et al. (2001) "Oral Cancer In Vivo Gene Expression Profiling Assisted By Laser Capture Microdissection And Microarray Analysis," *Oncogene* 20:6196-6204; Luo, J. H. et al. (2002) "Gene Expression Analysis Of Prostate Cancer," *Mol. Carcin.* 33:2535; Jiang, Y. et al. (2002) "Discovery Of Differentially Expressed Genes In Human Breast Cancer Using Subtracted cDNA Libraries And cDNA Microarrays," *Oncogene* 21:2270-2282; Scheidl, S. J. et al. (2002) "mRNA Expression Profiling Of Laser Microbeam Microdissected Cells From Slender Embryonic Structures," *Amer. J. of Pathol.* 160:801-813; Amundson, S. A. et al. (1999) "Fluorescent cDNA Microarray Hybridization Reveals Complexity And Heterogeneity Of Cellular Genotoxic Responses," *Oncogene* 18:3666-3672; Clark, J. et al. (2002) "Identification Of Amplified And Expressed Genes In Breast Cancer By Comparative Hybridization Onto Micro Arrays Of Randomly Selected cDNA Clones," *Genes, Chrom. and Cancer* 34:104-114; Rajeevan, M. S. et al. (2001) "Validation Of Arraybased Gene Expression Profiles By Real-Time (Kinetic) RT-PCR," *J. of Molec. Diagnos.* 3:26-31; Ross, D. T. et al. (2000) "Systematic Variation In Gene Expression Patterns In Human Cancer Cell Lines," *Nat. Genet.* 24:227-235; Taniguchi, M. et al. (2001) "Quantitative Assessment Of DNA Microarrays—Comparison With Northern Blot Analyses," *Genomics* 71:34-39; Sgroi, D. C. et al. (1999) "In Vivo Gene Expression Profile Analysis Of Human Breast Cancer Progression," *Cancer Res.* 59:5656-5661; Vu, H. L. et al. (2000) "A Method For Quantification Of Absolute Amounts Of Nucleic Acids By (RT)-PCR And A New Mathematical Model For Data Analysis," *Nucleic Acids Res.* 28:E18; Nacht, M. et al. (2001) "Molecular Characteristics Of Non-Small Cell Lung Cancer," *Proc. Natl. Acad. Sci. USA* 98:15203-15208). Real-time RT-PCR is the choice of many for quantitatively measuring specific mRNAs as, once established, the method is rapid, relatively inexpensive and requires minimal starting template (Rajeevan, M. S. et al. (2001) "Validation Of Arraybased Gene Expression Profiles By Real-Time (Kinetic) RT-PCR," *J. of Molec. Diagnos.* 3:26-31; Walker, N. (2002) "A Technique Whose Time Has Come," *Science* 296:557-558. However, it should be noted that real-time RT-PCR requires a significant amount of up-front effort to optimize amplification conditions, and there are potential pitfalls of the method that should be carefully monitored in order to obtain optimal results.

Comparisons of array-based results with northern blots reveal good general agreement between the methods, although arrays were less sensitive in measuring a subset of genes (Taniguchi, M. et al. (2001) "Quantitative Assessment Of DNA Microarrays—Comparison With Northern Blot Analyses," *Genomics* 71:34-39). Rajeevan and co-workers used a modified real-time RT-PCR method to evaluate array data (Rajeevan, M. S. et al. (2001) "Validation Of Arraybased GENE EXPRESSION PROFILES BY REAL-TIME (KINETIC) RT-PCR," *J. of Molec. Diagnos.* 3:26-31). These investigators also found that the majority of array results were qualitatively accurate; however, consistent validation was not achieved for genes showing less than a four-fold difference on the array. Moreover, for many genes examined, there were significant quantitative differences between array- and RT-PCR-based data. Overall, a review of the literature suggests that several technical questions regarding methods used for validation have yet to be thoroughly and rigorously addressed by the array community.

The selection of the gene set for follow-up analysis in the laboratory depends on the aim(s) of the study, but is influenced by factors such as the relative difference in expression among the samples, biological function, abundance levels, and availability of appropriate reagents (probes and antibodies). Investigators often choose the genes with the highest differential expression ratios, as these are most likely to be validated. However, since quantitative information from arrays may be imprecise for transcripts showing small expression differences, this strategy could overlook significant genes of interest. In the future, it is likely that development of more robust and quantitative array platforms will increase the confidence that genes exhibiting relatively small expression difference among samples are accurate and thus worth further investigation. In the near term, genes on an array that show significant differences in expression may serve as important clues and point investigators towards biochemical pathways whose members should be studied in detail using more quantitative methods.

In addition to validating array results at the mRNA level, it is equally desirable to evaluate expression levels of the corresponding protein products. At present, the frequency with which protein expression equates with transcript levels as measured on arrays is not clear. A poll of users of tissue micro arrays produced by the National Cancer Institute (see the website with a host name of "www", domain name "cancer.gov", and file extension "tarp") indicates that protein expression changes correlate with mRNA alterations less than 50% of the time. However, there are several caveats to consider that may be responsible for this discrepancy, including; the sensitivity and dynamic range of the methodology employed, the specificity of the antibody probe, the absolute difference in protein levels as compared to mRNA levels, and the abundance level of the protein being analyzed. Moreover, as indicated above, investigators often bias their selection of mRNAs for follow-up analysis towards those that show the largest fold-change. This may not necessarily translate to a similar difference at the protein level, particularly since protein function in the cell is affected by several parameters besides abundance.

Universality of Results Once array data have been analyzed and independently verified, either in silica or in the laboratory, investigators can determine if the expression profiles are a universal feature of the biological phenomenon under study. This question can be addressed by evaluating a critical gene set in a larger and more extensive study group, and can be performed either in silica or in the laboratory. For example, an investigator may identify a particular expression pattern in a breast cancer cell line after treatment with a drug. Subsequent experiments to evaluate the expression profiles of additional breast cancer cell lines are then desirable to determine if this finding represents a general feature of breast tumor cells. If so, a logical next step would be to examine the expression profiles in clinical samples from patients being treated with the drug. These experiments are important to validate or invalidate the data generated with an in vitro model system. Moreover, correlation of the gene expression pattern may also be made with respect to additional clinical parameters, such as the frequency with which patients show the identified profile, patient age, disease stage, and tumor histopathology (see, Singh, D. et al. (2002) "GENE EXPRESSION CORRELATES OF CLINICAL PROSTATE CANCER," *Cancer Cell* 1:203-209)

Tissue micro arrays (TMA) are an excellent approach for validation of array data in a large set of human or animal species (Dhanasekaran, S. M. et al. (2001) "DELINEATION OF PROGNOSTIC BIOMARKERS IN PROSTATE CANCER," *Nature* 412:822-826; Bangur, C. S. et al. (2002) "IDENTIFICATION OF GENES OVER-EXPRESSED IN SMALL CELL LUNG CARCINOMA USING SUPPRESSION SUBTRACTIVE HYBRIDIZATION AND cDNA MICROARRAY EXPRESSION ANALYSIS," *Oncogene* 21:3814-3825; Kononen, J. et al. (1998) "TISSUE MICRO ARRAYS FOR HIGH-THROUGHPUT MOLECULAR PROFILING OF TUMOR SPECIMENS," *Nat Med* 4:844-847; Kallioniemi, O. P. et al. (2001) "TISSUE MICROARRAY TECHNOLOGY FOR HIGH-THROUGHPUT MOLECULAR PROFILING OF CANCER," *Human Molec. Genet.* 10:657-662; Hoos, A. et al. "TISSUE MICRO ARRAY PROFILING OF CANCER SPECIMENS AND CELL LINES: OPPORTUNITIES AND LIMITATIONS," *Lab. Invest.* 81:1331-1338; Fejzo, M. et al. (2001) "FROZEN TUMOR TISSUE MICRO ARRAY TECHNOLOGY FOR ANALYSIS OF TUMOR RNA, DNA, AND PROTEINS," *Am. J. Pathol.* 159:1645-1650; Bubendorf, L. et al. (1999) "HORMONE THERAPY FAILURE IN HUMAN PROSTATE CANCER: ANALYSIS BY COMPLEMENTARY DNA AND TISSUE MICROARRAYS," *J. Natl. Canc. Inst.* 91:17581764; Battifora, H. (1986) "THE MULTITUMOR (SAUSAGE) TISSUE BLOCK: NOVEL METHOD FOR IMMUNOHISTOCHEMICAL ANTIBODY TESTING," *Lab. Invest.* 55:244-248). A TMA is a slide containing dozens to hundreds of pre-defined microscopic sections of tissue, making it feasible for an investigator to measure DNA, mRNA or protein expression in a large number of samples, providing enough statistical power for meaningful analysis. A particular advantage of the method is that both same-sample and new-sample analysis can be performed using the same TMA. A related approach is the "tissue lysate array," where lysates from cell populations collected by laser capture microdissection (LCM) are arrayed on a nylon coated slide (Emmert-Buck, M. R. et al. (1996) "LASER CAPTURE MICRODISSECTION," *Science* 274:998-1001; Bonner, R. F. et al. (1997) "LASER CAPTURE MICRODISSECTION: MOLECULAR ANALYSIS OF TISSUE," *Science* 278:1481-1483; Paweletz, C. P. et al. (2001) "REVERSE PHASE PROTEIN MICRO ARRAYS WHICH CAPTURE DISEASE PROGRESSION SHOW ACTIVATION OF PRO-SURVIVAL PATHWAYS AT THE CANCER INVASION FRONT," *Oncogene* 20:1981-1989). The most common methodology applied to TMAs is IHC, but increasingly ISH is being used, although sensitivity remains a challenging issue for ISH and frequently requires the use of radioactive probes for detection. Other techniques applicable to TMAs include fluorescence in-situ hybridization (FISH) for chromosomal copy number, and immunofluorescence in combination with confocal microscopy.

Like any experimental platform, TMAs are not without limitation. The most significant drawbacks involve sensitivity, lack of quantitation, and potential selection bias of the tissue samples. Both IHC and ISH are qualitative/semi-quantitative. With several hundred tissue specimens per TMA slide, the requirement for a pathologist or experienced investigator to view and score each sample is problematic. Robust methods to analyze TMA slides in an automated fashion are facilitated by the development of a TMA database exchange (website with host name of "wv", domain name of "lw.pathinfo.com", and file extension "iib/tmafaqvl.htm"). Selection bias is also a potential problem for TMAs due to the small size of the tissue core that is removed from the donor specimen. In some instances, the issue is of little concern as the expression levels of certain mRNAs and proteins are relatively uniform throughout the tissue. However, tissues are complex, multi-cellular entities that can contain significant intra-specimen molecular heterogeneity, particularly with respect to evolving disease processes. Therefore, a single small punch of tissue may not necessarily be representative of the overall state of the organ. Moreover, many small, but critically important structures (normal and disease-associated), are often sectioned through within the first few slides generated from a TMA block, and are thus unavailable for further study. Layered Expression Scanning, as described above, overcomes many problems related to sample bias.

Issues of cross-hybridization and RNA amplification related to validation of array data merit further discussion:

Non-specific and Cross Hybridization Two phenomena of cDNA microarrays related to target-probe hybridization have been observed (Emmert-Buck, M. R et al. (2000) "MOLECULAR PROFILING OF CLINICAL TISSUE SPECIMENS: FEASIBILITY AND APPLICATIONS," Am. J. of Pathol. 156:1109-1115). With many array systems, a significant number of arrayed DNAs produce "non-specific" background signals during experiments, mediated by repetitive elements, polyA tails, common motifs, or other unknown sequence-dependent regions of the DNA. When co-hybridized with two cDNA samples labeled with different fluorophores, these arrayed DNAs produce (often strong) signals that are interpreted as "equally expressed" in the biological samples under study. There are several important implications of this occurrence. For example, it can mislead investigators with respect to how many genes are actually being measured in an experiment. This is particularly important when assessing the effectiveness of an amplification scheme. If the criterion used to assess amplification efficiency is correlation of array results between amplified and non-amplified samples, and a large proportion of the similarity is due to non-specific hybridization, then the correlation coefficient between the ±amplification samples will be artificially high. Moreover, if this phenomenon is not factored into validation studies, investigators may find a significant discrepancy between array data and the expression results generated in subsequent follow-up efforts.

Non-specific signals on an array can also mislead investigators who are interested in the overall (in)activation state of a particular biochemical pathway. When comparing two samples, it is not only important to know which genes in a pathway are differentially expressed, it is also important to know which genes are not expressed. Erroneous data will compromise efforts to understand how each of the members of a pathway is regulated with respect to a particular cellular process. Finally, correlation of mRNA levels measured on an array with corresponding proteins will appear artificially low if, in fact, a substantial fraction of the "expressed genes" are due to experimental artifact. This can have important implications for efforts in which both protein expression—and lack of expression—are important. An example would be a search of candidate proteins for a tumor vaccine. Investigators often screen mRNA databases generated from arrays as an initial guide, with the intent to find proteins that are present in a target disease, but are not in normal cells and organs throughout the body. In this instance, non-specific array signals will make it appear that a significant number of genes are expressed widely in tissues when, in reality, their profile may be much more limited.

The second observed phenomenon is that a subset of target cDNAs will hybridize strongly to both their intended DNA probe, as well as other DNA probes on an array, ranging from a few to several dozen. In some cases, this can be understood based on sequence homologies among gene family members; however, it has been empirically observed that certain cDNAs will hybridize to arrayed DNA that do not share an easily identifiable common sequence. When these cDNAs are present at high copy number in a sample, they can produce artifactual data based on cross-hybridization. This phenomenon impacts upon investigators performing cluster analysis (i.e., examining gene sets that appear to share similar expression patterns and co-segregate during experiments). It is important that subsequent validation studies are designed with this possibility in mind. For example, follow-up studies using ISH analysis of TMAs could be similarly compromised by target-probe cross-hybridization. Thus, array cluster results should be verified using a methodology that does not rely on hybridization, or alternatively, using a northern blot where hybridization specificity can be evaluated based on transcript size. Additionally, to further validate their data, investigators can compare and contrast their array-based results in silico with expression information from sequencing-based profiling efforts that do not rely on hybridization methods, for example, expressed sequence tag (EST) or serial analysis of gene expression (SAGE) data sets.

Amplification of mRNA Samples One of the goals of the NCI's Cancer Genome Anatomy Project (CGAP) is to assess the feasibility of producing a complex transcriptome from small numbers of microdissected cells (website with host name of "cgap" and domain name of "nci.nih.gov"). A further aim was to evaluate the effects of PCR amplification on the mRNA population. Overall, it was observed that PCR induced a bias in transcript levels to a varying degree, depending on the amplification scheme, cycle number, and primer set. However, it was also found that "intentionally biasing" the transcriptome with PCR was useful for discovering novel expression differences between cell populations. The newly discovered genes were typically expressed at low abundance levels and were not identified in experiments using non-biased cDNA. Thus, as a general strategy, it may be necessary to include a selective amplification step in some array experiments such that low-abundance transcripts can be studied. However, if this strategy is utilized, investigators must then be aware that subsequent validation experiments will be more challenging, and may also require PCR-based approaches. In other words, the identified transcripts of interest may be difficult to measure using northern blots or other techniques that do not incorporate an amplification step. Moreover, evaluation of the corresponding protein products may be particularly demanding if they are similarly expressed at low levels in the biological samples under study.

Even though mRNA amplification may induce some bias in the transcriptome, several investigators have successfully used this approach to perform assay experiments (Sgroi, D. C. et al. (1999) "IN VIVO GENE EXPRESSION PROFILE ANALYSIS OF HUMAN BREAST CANCER PROGRESSION," Cancer Res. 59:5656-5661; Cole, K. A., et al. (1999) "THE GENETICS OF CANCER—A 3D MODEL," Nat. Genet. 21:38-41; Luo, L. et al. (1999) "GENE EXPRESSION PROFILES OF LASER-CAPTURED ADJACENT NEURONAL SUBTYPES," Nat. Med. 5:117-122; Luzzi, V. et al. (2001) "EXPRESSION PROFILING OF DUCTAL CARCINOMA IN SITU BY LASER CAPTURE MICRODISSECTION AND HIGH-DENSITY OLIGONUCLEOTIDE ARRAYS," Amer. L. Pathol. 158:2005-2010; Leethanakul, C. et al. (2000) "DISTINCT PATTERN OF EXPRESSION OF DIFFERENTIATION AND GROWTH-RELATED GENES IN SQUAMOUS CELL CARCINOMAS OF THE HEAD AND NECK REVEALED BY THE USE OF LASER CAPTURE MICRODISSECTION AND CDNA ARRAYS," Oncogene 19:3220-3224; Van Gelder, R. et al. (1990) "AMPLIFIED RNA SYNTHESIZED FROM LIMITED QUANTITIES OF HETEROGENEOUS CDNA," Proc. Natl. Acad. Sci. USA 87:1663-1667). Optimizing the method such that bias is consistent and reproducible is important, and allows relative comparisons of transcript levels between similarly prepared mRNA samples. However, one of the frequent problems that is observed is the inefficient priming of particular mRNA(s) early in the amplification process. This appears to occur randomly to individual transcripts. One approach to overcome this problem is to perform multiple (e.g., 3) independent amplifications of the starting mRNA, and subsequently pool the cDNA together for array analysis. Since drop-out occurs indiscriminately, it is unlikely that the same transcript will fail to amplify in more than one reaction. This approach is a simple means to reduce artifact and increases the percentage of expression differences that validate in follow-up studies.

The use of micro array and other global profiling technologies has lead to a significant number of exciting new biological discoveries, and important correlation between gene expression patterns and disease states. Nonetheless, it is important that investigators continue to optimize array methodologies, and develop new approaches to producing accurate and experimentally valid data. The techniques of "Expression Microdissection" (also referred to herein as Labeling-based ANalysis of Cells or "LANC"), and Layered Expression Scanning (LES) address this need. Both methods are conceptually simple and are intended to increase the throughput rate of experimentation, while decreasing the time and effort required of the researcher.

LES allows for multiplex measurement of transcripts or proteins in a variety of two-dimensional life science platforms (Englert, C. R. et al. (2000) "LAYERED EXPRESSION SCANNING: RAPID MOLECULAR PROFILING OF TUMOR SAMPLES," *Cancer Res.* 60:1526-1530). LES can be used to analyze gels, tissue sections, and cell populations recovered by LCM. The method is intended to facilitate the transition from global profiling efforts towards defined studies of biochemical pathways that are identified as important in array- and proteomic-based efforts. Two applications of LES technology are being used to validate expression data from the study of prostate cancer (Cole, K. A., et al. (1999) "THE GENETICS OF CANCER—A 3D MODEL," *Nat. Genet.* 21:38-41). The replicate gel approach for multiplex northern gels and immunoblots is being utilized for follow-up analysis of tumor-related mRNA and protein alterations, respectively. These blots permit robust quantitative measurement of expression levels, and include verification of probe specificity based on the molecular size of transcripts and proteins. In parallel, the mRNA and protein levels in whole-mount prostatectomy specimens are being analyzed using LES to validate and further characterize expression levels of genes identified in mRNA and protein profiling experiments (Emmert-Buck, M. R et al. (2000) "MOLECULAR PROFILING OF CLINICAL TISSUE SPECIMENS: FEASIBILITY AND APPLICATIONS," *Am. J. of Pathol.* 156:1109-1115; Ahram, M. et al. (2001) "PROTEOMIC ANALYSIS OF HUMAN PROSTATE CANCER," *Mol. Carcin.* 33: 9-15; Paweletz, C. P. et al. (2001) "REVERSE PHASE PROTEIN MICRO ARRAYS WHICH CAPTURE DISEASE PROGRESSION SHOW ACTIVATION OF PRO-SURVIVAL PATHWAYS AT THE CANCER INVASION FONT," *Oncogene* 20:1981-1989; Cole, K. A., et al. (1999) "THE GENETICS OF CANCER—A 3D MODEL," *Nat. Genet.* 21:38-41; Emmert-Buck, M. R et al. (2000) "AN APPROACH TO PROTEOMIC ANALYSIS OF HUMAN TUMORS," *Mol. Carcin.* 27:158-165; Ornstein, D. K. et al. (2000) "PROTEOMIC ANALYSIS OF LASER CAPTURE MICRODISSECTED PROSTATE CANCER AND IN VITRO CELL LINES," *Electrophoresis* 21:2235-2242; Carlisle, A. et al. (2000) "DEVELOPMENT OF A PROSTATE CDNA MICRO ARRAY AND STATISTICAL GENE EXPRESSION ANALYSIS PACKAGE," *Mol. Carcin.* 27:1-11; Strausberg, R L. et al. (2000) "THE CANCER GENOME ANATOMY PROJECT: BUILDING AN ANNOTATED GENE INDEX," *Trends in Genet.* 16:103-106; Paweletz, C. P. et al. (2002) "LOSS OF ANNEXIN I CORRELATES WITH EARLY ONSET OF TUMORIGENESIS IN ESOPHAGEAL AND PROSTATE CARCINOMA," *Cancer Res.* 60:6293-6297; Kang, J. et al. (2002) "DYSREGULATION OF ANNEXIN I PROTEIN EXPRESSION IN HIGH-GRADE PROSTATIC INTRAEPITHELIAL NEOPLASIA AND PROSTATE CANCER," *Clin. Cancer Res.* 8:117-123). This permits candidate prostate cancer-associated changes that were initially identified in a small set of cases to be (in)validated in a large number of specimens. Moreover, expression profiles can be assessed in all cell populations present (various tumor grades, pre-malignant lesions, normal epithelium, and lymphocytes associated with tumors cells), facilitating a more thorough investigation of the identified gene set in the disease process.

"Expression Microdissection" (LANC) is a front-end method for performing "virtual microdissection" of a specific cell type within a heterogeneous environment, based on expression of a target molecule. The approach is intended to improve the accuracy of global expression measurements, such that the data produced are robust and valid. Expression Microdissection (LANC) is performed using a specially designed polymer tethered to an antibody (or nucleic acid) for cell targeting, and to an enzyme for subsequent labeling of nucleic acids or proteins. The polymer is tethered to both a secondary antibody and a labeling enzyme. The polymer complex is hybridized to a primary antibody that is used to target a cell population of interest, followed by an enzymatic reaction that specifically labels the nucleic acids or proteins in the targeted cells. A portion of, or more preferably, the entire, tissue section is then scraped into a tube containing lysis buffer, and the labeled biomolecules analyzed by an appropriate detection method. The Expression Microdissection (LANG) procedure may be modified so as to employ it in conjunction with LCM (for example, by replacing the "labeling enzyme" with a dye (or dye-generating enzyme) that can activate the capture film). This approach may be useful when an investigator needs to physically procure biomolecules from a relatively large number of targeted cells. Once the polymer has been hybridized to the cell type of interest, the enzyme catalyzes a reaction that adds a label specifically to the biomolecules of the targeted cells. For example, reverse transcriptase can be used to create fluorescently labeled cDNA for arrays, or lactoperoxidase can be used to add $^{125}$I to proteins. After the enzymatic reaction, the entire biological sample is placed into a tube for analysis, utilizing a detection method in which only the labeled transcriptome or proteome is visualized. For experiments using targeting of cellular proteins, the polymer is linked to a secondary antibody, thus allowing the investigator to employ any primary antibody of interest in their experiment. LES, Expression Microdissection (LANC), LCM, and immuno-LCM can be important and complementary tools that will assist investigators in phenotype- and expression-based profiling studies of cell populations (Emmert-Buck, M. R. et al. (1996) "LASER CAPTURE MICRODISSECTION," *Science* 274:998-1001; Bonner, R. F. et al. (1997) "LASER CAPTURE MICRODISSECTION: MOLECULAR ANALYSIS OF TISSUE," *Science* 278:1481-1483; Fend, F. et al. (1999) "IMMUNO-LCM: LASER CAPTURE MICRODISSECTION OF IMMUNOSTAINED FROZEN SECTIONS FOR MRNA ANALYSIS," *Amer. J. Pathol.* 154:61-66).

EXAMPLE 5

Use of EMI Devices in Conjunction with Agarose Gel Spin Transfer Procedures

Spin transfer is a method that can be employed to move biomolecules out of a gel. In accordance with this procedure, fluid is recovered from a gel or other matrix through centrifugation. The EMI devices of the present invention can be used in conjunction with such spin transfer procedures to facilitate the recovery of biomolecules (FIG. 5). To illustrate this aspect of the invention, a sample containing human papilloma virus is subjected to amplification using the polymerase chain reaction (PCR). After 40 PCR cycles, the PCR-amplified material is subjected to tris-boric acid (TB) agarose gel electrophoresis using standard protocols.

The resulting "initial" gel is then placed on top of a mesh screen that has been placed on a 384-well EMI plate and the combination is spun at 2,000 rpms for 2 minutes in a swinging bucket centrifuge rotor (e.g., a Sorval® RT7+ rotor). The centrifugation serves to extract fluid from the gel and deposit it into the microwells of the EMI plate; the screen serves to support the gel during the centrifugation and to minimize the transfer of agarose into the microwells.

Figure 6A:
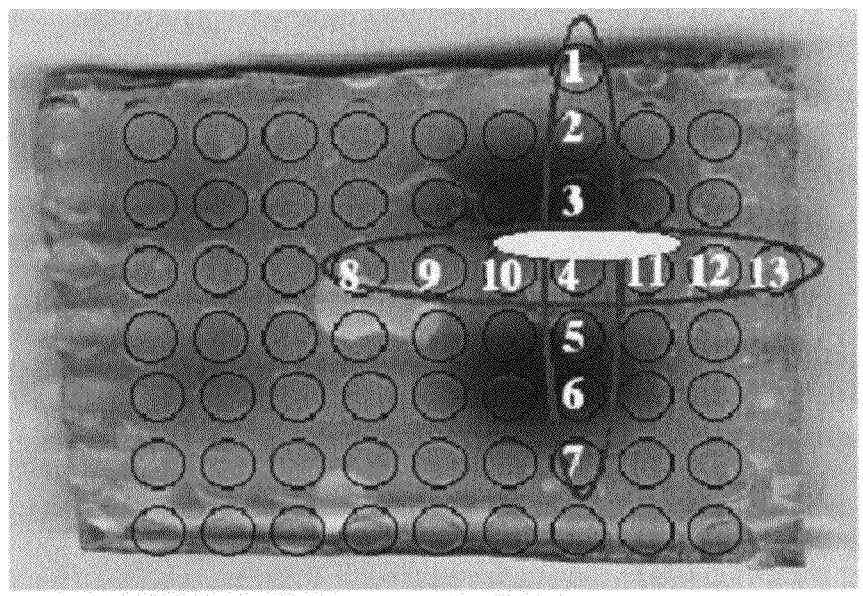
FIGS. 6A and 6B illustrate results obtaining using the EMI apparatus of the present invention in combination with agarose gel spin transfer.
Figure 6B:
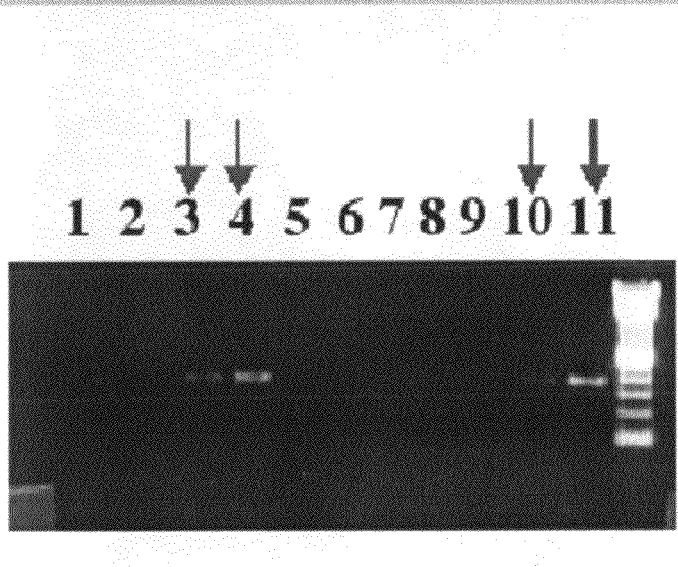

After such centrifugation, the gel is then removed from the EMI plate and 1 μl samples are extracted from the transferred fluid corresponding to the wells indicated in the second image (FIG. 6A; solid oval). Using the transferred fluid as the template, the samples are then re-amplified for the human papilloma virus band. Only the wells containing the band demonstrate the PCR amplification product upon subsequent electrophoretic analysis (FIG. 6B; indicated by arrows). The experiment demonstrates that the EMI plate retains the two-dimensional architecture of the initial agarose gel.

It is preferable to employ a tris borate (TB) buffer in the above procedure instead of a tris borate EDTA (TBE) buffer in order to avoid introduction of the magnesium chelator, EDTA, which could potentially impair the PCR amplification step. Alternatively, if one desires to employ TBE buffer, an excess of magnesium can be employed or added, if needed All publications and patents mentioned in this specification are herein incorporated by reference to the same extent as if each individual publication or patent application was specifically and individually indicated to be incorporated by reference.

While the invention has been described in connection with specific embodiments thereof, it will be understood that it is capable of further modifications and this application is intended to cover any variations, uses, or adaptations of the invention following, in general, the principles of the invention and including such departures from the present disclosure as come within known or customary practice within the art to which the invention pertains and as may be applied to the essential features hereinbefore set forth.

We claim:

1. A method for determining the location(s) of one or more biomolecules present within a sample wherein the biomolecules have a 2-dimensional relationship to each other in the sample, comprising:
    positioning the sample with respect to an External Movement Inhibitor (EMI) device while preserving the relative 2-dimensional relationship of the biomolecules to each other, wherein the EMI device comprises a plurality of wells or a plurality of through-holes and a plurality of needles or probes;
    sequestering the one or more biomolecules from specific regions of the sample in the plurality of wells or the plurality of through-holes of the EMI device while preserving the relative 2-dimensional relationship of the biomolecules to each other, such that the biomolecules in the locations in the EMI device have the same relative spatial positions that they had in the sample prior to sequestering them in the EMI device;
    manipulating the one or more sequestered biomolecules within the plurality of wells or through-holes of the EMI device while preserving the relative 2-dimensional relationship of the biomolecules to each other, wherein manipulating comprises nucleic acid amplification, reverse transcription, cloning, or a combination of two or more thereof; and
    determining the location of one or more wells or through-holes in the EMI device which contain the one or more preselected biomolecules, thereby permitting a determination of the locations in the sample in which the preselected biomolecules were present.

2. The method of claim 1, wherein the one or more preselected biomolecules are nucleic acid molecules.

3. The method of claim 2, wherein the one or more preselected nucleic acid molecules are diagnostic of a disease state.

4. The method of claim 1, wherein the nucleic acid amplification comprises performing a polymerase chain reaction.

5. The method of claim 1, wherein the EMI device is one of a microwell plate or a microtiter plate with a plurality of needles or probes.

6. The method of claim 1, wherein sequestering the one or more biomolecules comprises transferring fluid containing biomolecules from regions of the sample to correspondingly positioned holes or wells in the EMI device.

7. The method of claim 6, wherein sequestering the one or more biomolecules comprises placing the sample onto a mesh screen, placing the mesh screen onto the EMI device, and centrifuging the sample, mesh screen and EMI device such that the fluid from the sample is deposited into the holes or wells of the EMI device.

8. The method of claim 1, wherein sequestering the one or more biomolecules from specific regions of the sample within the EMI device comprises punching the sample with a grid such that specific regions of the sample are deposited into the plurality of holes or plurality of wells of the EMI device while preserving the relative 2-dimensional relationship of the biomolecules as existed in the sample prior to punching the sample.

9. The method of claim 1, wherein the sample is a tissue section, a gel containing biomolecules, a membrane containing biomolecules, an adhesive film with cells adhered to some regions of the surface, or a tissue micro-array.

10. The method of claim 1, wherein the manipulation is performed simultaneously on all of the plurality of wells or plurality of through-holes of the EMI device.

11. The method of claim 1, wherein the determination of the location of the one or more biomolecules is performed simultaneously on all of the plurality of wells or plurality of through-holes of the EMI device.

12. The method of claim 1, wherein positioning the sample comprises contacting the sample with the External Movement Inhibitor (EMI) device comprising the plurality of wells or the plurality of through-holes.

* * * * *